(12) United States Patent
Hushka et al.

(10) Patent No.: US 8,251,996 B2
(45) Date of Patent: Aug. 28, 2012

(54) INSULATING SHEATH FOR ELECTROSURGICAL FORCEPS

(75) Inventors: Dylan Hushka, Chandler, AZ (US); Paul Guerra, Los Gatos, CA (US)

(73) Assignee: TYCO Healthcare Group LP, Mansfield, MA (US)

( * ) Notice: Subject to any disclaimer, the term of this patent is extended or adjusted under 35 U.S.C. 154(b) by 1009 days.

(21) Appl. No.: 12/235,846

(22) Filed: Sep. 23, 2008

(65) Prior Publication Data

US 2009/0088747 A1  Apr. 2, 2009

Related U.S. Application Data

(60) Provisional application No. 60/995,866, filed on Sep. 28, 2007.

(51) Int. Cl.
*A61B 18/14* (2006.01)
(52) U.S. Cl. .......................... 606/51; 606/52
(58) Field of Classification Search .......... 606/32, 606/51, 52, 206–209; 607/98, 100, 115
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |

(Continued)

FOREIGN PATENT DOCUMENTS

CA  2104423  2/1994

(Continued)

OTHER PUBLICATIONS

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(Continued)

*Primary Examiner* — Michael Peffley
*Assistant Examiner* — Thomas Giuliani

(57) ABSTRACT

An electrosurgical forceps includes a shaft having a pair of jaw members at a distal end movable about a pivot from a first position disposed in spaced relation relative to one another to a second position wherein the jaw members are closer to one another for grasping tissue. One or both of the jaw members are adapted to connect to a source of electrical energy such that the jaw members are capable of conducting electrical energy to tissue held therebetween. An insulative sheath is fitted for removal atop at least a portion of an exterior surface of one or both jaw members, about the pivot and the distal end of the shaft. The insulative sheath houses a silicone lube configured to facilitate insertion of the forceps through a cannula after removal of the insulative sheath.

10 Claims, 18 Drawing Sheets

U.S. PATENT DOCUMENTS

| | | | |
|---|---|---|---|
| 2,796,065 A | 6/1957 | Kapp | |
| 3,073,311 A | 1/1963 | Tibbs et al. | |
| 3,372,288 A | 3/1968 | Wigington | |
| 3,459,187 A | 8/1969 | Pallotta | |
| 3,643,663 A | 2/1972 | Sutter | |
| 3,648,001 A | 3/1972 | Anderson et al. | |
| 3,651,811 A | 3/1972 | Hildebrandt et al. | |
| 3,678,229 A | 7/1972 | Osika | |
| 3,720,896 A | 3/1973 | Beierlein | |
| 3,763,726 A | 10/1973 | Hildebrand | |
| 3,779,918 A | 12/1973 | Ikeda et al. | |
| 3,801,766 A | 4/1974 | Morrison, Jr. | |
| 3,862,630 A | 1/1975 | Balamuth | |
| 3,863,339 A | 2/1975 | Reaney et al. | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,016,881 A | 4/1977 | Rioux et al. | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,076,028 A | 2/1978 | Simmons | |
| 4,080,820 A | 3/1978 | Allen | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,187,420 A | 2/1980 | Piber | |
| 4,233,734 A | 11/1980 | Bies | |
| 4,236,470 A | 12/1980 | Stenson | |
| 4,300,564 A | 11/1981 | Furihata | |
| 4,311,145 A | 1/1982 | Esty et al. | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,443,935 A | 4/1984 | Zamba et al. | |
| 4,452,246 A | 6/1984 | Bader et al. | |
| 4,470,786 A | 9/1984 | Sano et al. | |
| 4,492,231 A | 1/1985 | Auth | |
| 4,493,320 A | 1/1985 | Treat | |
| 4,503,855 A | 3/1985 | Maslanka | |
| 4,506,669 A | 3/1985 | Blake, III | |
| 4,509,518 A | 4/1985 | McGarry et al. | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,624,254 A | 11/1986 | McGarry et al. | |
| 4,655,215 A | 4/1987 | Pike | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Koch et al. | |
| 4,733,662 A | 3/1988 | DeSatnick et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,829,313 A | 5/1989 | Taggart | |
| 4,846,171 A | 7/1989 | Kauphusman et al. | |
| 4,887,612 A | 12/1989 | Esser et al. | |
| 4,938,761 A | 7/1990 | Ensslin | |
| 4,947,009 A | 8/1990 | Osika et al. | |
| 4,985,030 A | 1/1991 | Melzer et al. | |
| 5,007,908 A | 4/1991 | Rydell | |
| 5,026,370 A | 6/1991 | Lottick | |
| 5,026,371 A | 6/1991 | Rydell et al. | |
| 5,035,695 A | 7/1991 | Weber, Jr. et al. | |
| 5,037,433 A | 8/1991 | Wilk et al. | |
| 5,042,707 A | 8/1991 | Taheri | |
| 5,047,046 A | 9/1991 | Bodoia | |
| 5,078,716 A | 1/1992 | Doll | |
| 5,084,057 A | 1/1992 | Green et al. | |
| 5,085,659 A | 2/1992 | Rydell | |
| 5,099,840 A | 3/1992 | Goble et al. | |
| 5,100,430 A | 3/1992 | Avellanet et al. | |
| 5,108,392 A | 4/1992 | Spingler | |
| 5,112,343 A | 5/1992 | Thornton | |
| 5,116,332 A | 5/1992 | Lottick | |
| 5,147,357 A | 9/1992 | Rose et al. | |
| 5,151,102 A | 9/1992 | Kamiyama et al. | |
| 5,151,978 A | 9/1992 | Bronikowski et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,209,747 A | 5/1993 | Knoepfler | |
| 5,211,655 A | 5/1993 | Hasson | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A * | 11/1993 | Phillips et al. | 606/140 |
| 5,275,615 A | 1/1994 | Rose | |
| 5,277,201 A | 1/1994 | Stern | |
| 5,282,799 A | 2/1994 | Rydell | |
| 5,282,800 A | 2/1994 | Foshee et al. | |
| 5,282,826 A | 2/1994 | Quadri | |
| 5,290,286 A | 3/1994 | Parins | |
| 5,300,082 A | 4/1994 | Sharpe et al. | |
| 5,304,203 A | 4/1994 | El-Mallawany et al. | |
| 5,308,353 A | 5/1994 | Beurrier | |
| 5,308,357 A | 5/1994 | Lichtman | |
| 5,313,027 A | 5/1994 | Inoue et al. | |
| 5,314,445 A | 5/1994 | Degwitz et al. | |
| 5,318,589 A | 6/1994 | Lichtman | |
| 5,324,289 A | 6/1994 | Eggers | |
| D348,930 S | 7/1994 | Olson | |
| 5,326,806 A | 7/1994 | Yokoshima et al. | |
| 5,330,471 A | 7/1994 | Eggers | |
| 5,330,502 A | 7/1994 | Hassler et al. | |
| 5,334,166 A * | 8/1994 | Palestrant | 604/265 |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,350,391 A | 9/1994 | Iacovelli | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,374,277 A | 12/1994 | Hassler | |
| 5,376,089 A | 12/1994 | Smith | |
| 5,383,875 A | 1/1995 | Bays et al. | |
| 5,383,897 A | 1/1995 | Wholey | |
| 5,389,098 A | 2/1995 | Tsuruta et al. | |
| 5,389,103 A | 2/1995 | Melzer et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,403,342 A | 4/1995 | Tovey et al. | |
| 5,405,344 A | 4/1995 | Williamson et al. | |
| 5,409,763 A | 4/1995 | Serizawa et al. | |

| | | | | | |
|---|---|---|---|---|---|
| 5,411,519 A | 5/1995 | Tovey et al. | 5,603,723 A | 2/1997 | Aranyi et al. |
| 5,411,520 A | 5/1995 | Nash et al. | 5,611,798 A | 3/1997 | Eggers |
| 5,413,571 A | 5/1995 | Katsaros et al. | 5,611,808 A | 3/1997 | Hossain et al. |
| 5,415,656 A | 5/1995 | Tihon et al. | 5,611,813 A | 3/1997 | Lichtman |
| 5,415,657 A | 5/1995 | Taymor-Luria | 5,620,415 A | 4/1997 | Lucey et al. |
| 5,422,567 A | 6/1995 | Matsunaga | 5,620,453 A | 4/1997 | Nallakrishnan |
| 5,423,810 A | 6/1995 | Goble et al. | 5,620,459 A | 4/1997 | Lichtman |
| 5,425,690 A | 6/1995 | Chang | 5,624,452 A | 4/1997 | Yates |
| 5,425,739 A | 6/1995 | Jessen | 5,626,578 A | 5/1997 | Tihon |
| 5,429,616 A | 7/1995 | Schaffer | 5,626,609 A | 5/1997 | Zvenyatsky et al. |
| 5,431,672 A | 7/1995 | Cote et al. | 5,630,833 A | 5/1997 | Katsaros et al. |
| 5,431,674 A | 7/1995 | Basile et al. | 5,637,110 A | 6/1997 | Pennybacker et al. |
| 5,437,292 A | 8/1995 | Kipshidze et al. | 5,638,003 A | 6/1997 | Hall |
| 5,438,302 A | 8/1995 | Goble | 5,643,294 A | 7/1997 | Tovey et al. |
| 5,439,478 A | 8/1995 | Palmer | 5,647,869 A | 7/1997 | Goble et al. |
| 5,441,517 A | 8/1995 | Kensey et al. | 5,647,871 A | 7/1997 | Levine et al. |
| 5,443,463 A | 8/1995 | Stern et al. | 5,649,959 A | 7/1997 | Hannam et al. |
| 5,443,464 A | 8/1995 | Russell et al. | 5,655,650 A | 8/1997 | Naitou |
| 5,443,480 A | 8/1995 | Jacobs et al. | 5,658,281 A | 8/1997 | Heard |
| 5,445,638 A | 8/1995 | Rydell et al. | D384,413 S | 9/1997 | Zlock et al. |
| 5,445,658 A | 8/1995 | Durrfeld et al. | 5,662,667 A | 9/1997 | Knodel |
| 5,449,480 A | 9/1995 | Kuriya et al. | 5,665,100 A | 9/1997 | Yoon |
| 5,451,224 A | 9/1995 | Goble et al. | 5,667,526 A | 9/1997 | Levin |
| 5,454,823 A | 10/1995 | Richardson et al. | 5,674,220 A | 10/1997 | Fox et al. |
| 5,454,827 A | 10/1995 | Aust et al. | 5,674,229 A | 10/1997 | Tovey et al. |
| 5,456,684 A | 10/1995 | Schmidt et al. | 5,681,282 A | 10/1997 | Eggers et al. |
| 5,458,598 A | 10/1995 | Feinberg et al. | 5,688,270 A | 11/1997 | Yates et al. |
| 5,460,629 A | 10/1995 | Shlain et al. | 5,690,652 A | 11/1997 | Wurster et al. |
| 5,461,765 A | 10/1995 | Linden et al. | 5,690,653 A | 11/1997 | Richardson et al. |
| 5,462,546 A | 10/1995 | Rydell | 5,693,051 A | 12/1997 | Schulze et al. |
| 5,472,442 A | 12/1995 | Klicek | 5,693,920 A | 12/1997 | Maeda |
| 5,472,443 A | 12/1995 | Cordis et al. | 5,695,522 A | 12/1997 | LeMaire, III et al. |
| 5,478,351 A | 12/1995 | Meade et al. | 5,700,261 A | 12/1997 | Brinkerhoff |
| 5,480,406 A | 1/1996 | Nolan et al. | 5,700,270 A | 12/1997 | Peyser et al. |
| 5,480,409 A | 1/1996 | Riza | 5,702,390 A | 12/1997 | Austin et al. |
| 5,484,436 A | 1/1996 | Eggers et al. | 5,707,369 A | 1/1998 | Vaitekunas et al. |
| 5,496,312 A | 3/1996 | Klicek | 5,709,680 A | 1/1998 | Yates et al. |
| 5,496,317 A | 3/1996 | Goble et al. | 5,716,366 A | 2/1998 | Yates |
| 5,496,347 A | 3/1996 | Hashiguchi et al. | 5,720,744 A | 2/1998 | Eggleston et al. |
| 5,499,997 A | 3/1996 | Sharpe et al. | 5,722,421 A | 3/1998 | Francese et al. |
| 5,509,922 A | 4/1996 | Aranyi et al. | 5,725,536 A | 3/1998 | Oberlin et al. |
| 5,512,721 A | 4/1996 | Young et al. | 5,727,428 A | 3/1998 | LeMaire, III et al. |
| 5,514,134 A | 5/1996 | Rydell et al. | 5,735,848 A | 4/1998 | Yates et al. |
| 5,527,313 A | 6/1996 | Scott et al. | 5,743,906 A | 4/1998 | Parins et al. |
| 5,528,833 A | 6/1996 | Sakuma | 5,752,973 A | 5/1998 | Kieturakis |
| 5,529,067 A | 6/1996 | Larsen et al. | 5,755,717 A | 5/1998 | Yates et al. |
| 5,531,744 A | 7/1996 | Nardella et al. | 5,759,188 A | 6/1998 | Yoon |
| 5,536,251 A | 7/1996 | Evard et al. | 5,766,130 A | 6/1998 | Selmonosky |
| 5,540,684 A | 7/1996 | Hassler, Jr. | 5,766,166 A | 6/1998 | Hooven |
| 5,540,685 A | 7/1996 | Parins et al. | 5,766,170 A | 6/1998 | Eggers |
| 5,540,706 A | 7/1996 | Aust et al. | 5,766,196 A | 6/1998 | Griffiths |
| 5,540,715 A | 7/1996 | Katsaros et al. | 5,769,849 A | 6/1998 | Eggers |
| 5,542,945 A | 8/1996 | Fritzsch | 5,772,655 A | 6/1998 | Bauer et al. |
| 5,558,671 A | 9/1996 | Yates | 5,772,670 A | 6/1998 | Brosa |
| 5,558,672 A | 9/1996 | Edwards et al. | 5,776,128 A | 7/1998 | Eggers |
| 5,562,619 A | 10/1996 | Mirarchi et al. | 5,776,130 A | 7/1998 | Buysse et al. |
| 5,562,699 A | 10/1996 | Heimberger et al. | 5,779,646 A | 7/1998 | Koblish et al. |
| 5,562,720 A | 10/1996 | Stern et al. | 5,779,701 A | 7/1998 | McBrayer et al. |
| 5,564,615 A | 10/1996 | Bishop et al. | H1745 H | 8/1998 | Paraschac |
| 5,569,241 A | 10/1996 | Edwardds | 5,792,137 A | 8/1998 | Carr et al. |
| 5,569,243 A | 10/1996 | Kortenbach et al. | 5,792,165 A | 8/1998 | Klieman et al. |
| 5,571,100 A | 11/1996 | Goble et al. | 5,792,177 A | 8/1998 | Kaseda |
| 5,573,424 A | 11/1996 | Poppe | 5,797,537 A | 8/1998 | Oberlin et al. |
| 5,573,534 A | 11/1996 | Stone | 5,797,927 A | 8/1998 | Yoon |
| 5,573,535 A | 11/1996 | Viklund | 5,797,938 A | 8/1998 | Paraschac et al. |
| 5,575,799 A | 11/1996 | Bolanos et al. | 5,797,941 A | 8/1998 | Schulze et al. |
| 5,575,805 A | 11/1996 | Li | 5,797,958 A | 8/1998 | Yoon |
| 5,578,052 A | 11/1996 | Koros et al. | 5,800,449 A | 9/1998 | Wales |
| 5,579,781 A | 12/1996 | Cooke | 5,807,393 A | 9/1998 | Williamson, IV et al. |
| 5,582,611 A | 12/1996 | Tsukagoshi et al. | 5,810,764 A | 9/1998 | Eggers et al. |
| 5,582,617 A | 12/1996 | Klieman et al. | 5,810,805 A | 9/1998 | Sutcu et al. |
| 5,585,896 A | 12/1996 | Yamazaki et al. | 5,810,808 A | 9/1998 | Eggers |
| 5,590,570 A | 1/1997 | LeMaire, III et al. | 5,810,811 A | 9/1998 | Yates et al. |
| 5,591,181 A | 1/1997 | Stone et al. | 5,810,877 A | 9/1998 | Roth et al. |
| 5,597,107 A | 1/1997 | Knodel et al. | 5,814,043 A | 9/1998 | Shapeton |
| 5,601,224 A | 2/1997 | Bishop et al. | 5,814,054 A | 9/1998 | Kortenbach et al. |
| 5,601,601 A | 2/1997 | Tal et al. | 5,817,093 A | 10/1998 | Williamson, IV et al. |
| 5,601,641 A | 2/1997 | Stephens | 5,817,119 A | 10/1998 | Klieman et al. |
| 5,603,711 A | 2/1997 | Parins et al. | 5,820,630 A | 10/1998 | Lind |

| Patent No. | Date | Inventor |
|---|---|---|
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | VanDeMoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |

| Patent No. | Date | Inventor |
|---|---|---|
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Lands et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |

| Patent/Pub No. | Date | Inventor |
|---|---|---|
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0247849 A1 | 12/2004 | Truckai |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271030 A1 | 11/2006 | Francis et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0027447 A1 | 2/2007 | Theroux et al. |
| 2007/0043352 A1 | 2/2007 | Garrison et al. |

| | | | | | | |
|---|---|---|---|---|---|---|
| 2007/0043353 A1 | 2/2007 | Dycus et al. | | DE | 2627679 | 1/1977 |
| 2007/0060919 A1 | 3/2007 | Isaacson et al. | | DE | 3612646 | 4/1987 |
| 2007/0062017 A1 | 3/2007 | Dycus et al. | | DE | 8712328 | 3/1988 |
| 2007/0074807 A1 | 4/2007 | Guerra | | DE | 4303882 | 8/1994 |
| 2007/0078456 A1 | 4/2007 | Dumbauld et al. | | DE | 4403252 | 8/1995 |
| 2007/0078458 A1 | 4/2007 | Dumbauld et al. | | DE | 19515914 | 7/1996 |
| 2007/0078459 A1 | 4/2007 | Johnson et al. | | DE | 29616210 | 1/1997 |
| 2007/0088356 A1 | 4/2007 | Moses et al. | | DE | 19608716 | 4/1997 |
| 2007/0106292 A1* | 5/2007 | Kaplan et al. ............ 606/41 | | DE | 19751106 | 5/1998 |
| 2007/0106295 A1 | 5/2007 | Garrison et al. | | DE | 19751108 | 5/1999 |
| 2007/0106297 A1 | 5/2007 | Dumbauld et al. | | DE | 19738457 | 1/2009 |
| 2007/0118111 A1 | 5/2007 | Weinberg | | EP | 0364216 | 4/1990 |
| 2007/0118115 A1 | 5/2007 | Artale et al. | | EP | 0467501 | 1/1992 |
| 2007/0142833 A1 | 6/2007 | Dycus et al. | | EP | 0518230 | 12/1992 |
| 2007/0142834 A1 | 6/2007 | Dumbauld | | EP | 0541930 | 5/1993 |
| 2007/0156139 A1 | 7/2007 | Schechter et al. | | EP | 0572131 | 12/1993 |
| 2007/0156140 A1 | 7/2007 | Baily | | EP | 0584787 | 3/1994 |
| 2007/0173811 A1 | 7/2007 | Couture et al. | | EP | 0589453 | 3/1994 |
| 2007/0173814 A1 | 7/2007 | Hixson et al. | | EP | 0589555 | 3/1994 |
| 2007/0179499 A1 | 8/2007 | Garrison | | EP | 0623316 | 11/1994 |
| 2007/0198011 A1 | 8/2007 | Sugita | | EP | 0624348 | 11/1994 |
| 2007/0213712 A1 | 9/2007 | Buysse et al. | | EP | 0650701 | 5/1995 |
| 2007/0255279 A1 | 11/2007 | Buysse et al. | | EP | 0694290 | 3/1996 |
| 2007/0260235 A1 | 11/2007 | Podhajsky | | EP | 0717966 | 6/1996 |
| 2007/0260238 A1 | 11/2007 | Guerra | | EP | 0754437 | 3/1997 |
| 2007/0260241 A1 | 11/2007 | Dalla Betta et al. | | EP | 0517243 | 9/1997 |
| 2007/0260242 A1 | 11/2007 | Dycus et al. | | EP | 0853922 | 7/1998 |
| 2007/0265616 A1 | 11/2007 | Couture et al. | | EP | 0875209 | 11/1998 |
| 2008/0004616 A1 | 1/2008 | Patrick | | EP | 0878169 | 11/1998 |
| 2008/0009860 A1 | 1/2008 | Odom | | EP | 0887046 | 1/1999 |
| 2008/0015575 A1 | 1/2008 | Odom et al. | | EP | 0923907 | 6/1999 |
| 2008/0021450 A1 | 1/2008 | Couture | | EP | 0986990 | 3/2000 |
| 2008/0033428 A1 | 2/2008 | Artale et al. | | EP | 1034747 | 9/2000 |
| 2008/0039835 A1 | 2/2008 | Johnson et al. | | EP | 1034748 | 9/2000 |
| 2008/0039836 A1 | 2/2008 | Odom et al. | | EP | 1025807 | 10/2000 |
| 2008/0045947 A1 | 2/2008 | Johnson et al. | | EP | 1034746 | 10/2000 |
| 2008/0058802 A1 | 3/2008 | Couture et al. | | EP | 1050278 | 11/2000 |
| 2008/0082100 A1 | 4/2008 | Orton et al. | | EP | 1053719 | 11/2000 |
| 2008/0091189 A1 | 4/2008 | Carlton | | EP | 1053720 | 11/2000 |
| 2008/0114356 A1 | 5/2008 | Johnson et al. | | EP | 1055399 | 11/2000 |
| 2008/0167651 A1 | 7/2008 | Tetzlaff et al. | | EP | 1055400 | 11/2000 |
| 2008/0195093 A1 | 8/2008 | Couture et al. | | EP | 1080694 | 3/2001 |
| 2008/0215051 A1 | 9/2008 | Buysse et al. | | EP | 1082944 | 3/2001 |
| 2008/0243120 A1 | 10/2008 | Lawes et al. | | EP | 1159926 | 12/2001 |
| 2008/0249527 A1 | 10/2008 | Couture | | EP | 1177771 | 2/2002 |
| 2008/0312653 A1 | 12/2008 | Arts et al. | | EP | 1301135 | 4/2003 |
| 2008/0319442 A1 | 12/2008 | Unger et al. | | EP | 1330991 | 7/2003 |
| 2009/0012520 A1 | 1/2009 | Hixson et al. | | EP | 1486177 | 6/2004 |
| 2009/0018535 A1 | 1/2009 | Schechter et al. | | EP | 1472984 | 11/2004 |
| 2009/0024126 A1 | 1/2009 | Artale et al. | | EP | 0774232 | 1/2005 |
| 2009/0043304 A1 | 2/2009 | Tetzlaff et al. | | EP | 1527747 | 5/2005 |
| 2009/0048596 A1 | 2/2009 | Shields et al. | | EP | 1530952 | 5/2005 |
| 2009/0062794 A1 | 3/2009 | Buysse et al. | | EP | 1532932 | 5/2005 |
| 2009/0082766 A1 | 3/2009 | Unger et al. | | EP | 1535581 | 6/2005 |
| 2009/0082767 A1 | 3/2009 | Unger et al. | | EP | 1609430 | 12/2005 |
| 2009/0082769 A1 | 3/2009 | Unger et al. | | EP | 1632192 | 3/2006 |
| 2009/0088738 A1 | 4/2009 | Guerra et al. | | EP | 1642543 | 4/2006 |
| 2009/0088739 A1 | 4/2009 | Hushka et al. | | EP | 1645238 | 4/2006 |
| 2009/0088740 A1 | 4/2009 | Guerra et al. | | EP | 1645240 | 4/2006 |
| 2009/0088741 A1 | 4/2009 | Hushka et al. | | EP | 1649821 | 4/2006 |
| 2009/0088744 A1 | 4/2009 | Townsend | | EP | 1707143 | 10/2006 |
| 2009/0088745 A1 | 4/2009 | Hushka et al. | | EP | 1769765 | 4/2007 |
| 2009/0088746 A1 | 4/2009 | Hushka et al. | | EP | 1769766 | 4/2007 |
| 2009/0088747 A1 | 4/2009 | Hushka et al. | | EP | 1929970 | 6/2008 |
| 2009/0088748 A1* | 4/2009 | Guerra et al. ............ 606/51 | | EP | 1683496 | 12/2008 |
| 2009/0088749 A1* | 4/2009 | Hushka et al. ............ 606/51 | | GB | 623316 | 5/1949 |
| 2009/0088750 A1 | 4/2009 | Hushka et al. | | GB | 1490585 | 11/1977 |
| 2009/0112206 A1 | 4/2009 | Dumbauld et al. | | GB | 2214430 A | 6/1989 |
| 2009/0131934 A1 | 5/2009 | Odom et al. | | GB | 2213416 A | 8/1989 |
| 2009/0149853 A1 | 6/2009 | Shields et al. | | JP | 61-501068 | 9/1984 |
| 2009/0149854 A1 | 6/2009 | Cunningham et al. | | JP | 65-502328 | 3/1992 |
| 2009/0171350 A1 | 7/2009 | Dycus et al. | | JP | 5-5106 | 1/1993 |
| 2009/0171353 A1 | 7/2009 | Johnson et al. | | JP | 5-40112 | 2/1993 |
| 2009/0182327 A1 | 7/2009 | Unger | | JP | 06343644 A2 | 12/1994 |
| 2009/0187188 A1 | 7/2009 | Guerra et al. | | JP | 07265328 A2 | 10/1995 |
| FOREIGN PATENT DOCUMENTS | | | | JP | 08056955 A2 | 3/1996 |
| | | | | JP | 08252263 A2 | 10/1996 |
| DE | 2415263 | 10/1975 | | JP | 09010223 A2 | 1/1997 |
| DE | 2514501 | 10/1976 | | JP | 11244298 A2 | 9/1999 |

| | | | |
|---|---|---|---|
| JP | 2000-342599 | A2 | 12/2000 |
| JP | 2000-350732 | A2 | 12/2000 |
| JP | 2001-008944 | A2 | 1/2001 |
| JP | 2001-029356 | A2 | 2/2001 |
| JP | 2001-128990 | A2 | 5/2001 |
| SU | 401367 | | 11/1974 |
| WO | WO 89/00757 | | 1/1989 |
| WO | WO 92/04873 | | 4/1992 |
| WO | WO 92/06642 | | 4/1992 |
| WO | WO 93/21845 | | 11/1993 |
| WO | WO 94/08524 | | 4/1994 |
| WO | WO 94/20025 | | 9/1994 |
| WO | WO 95/02369 | | 1/1995 |
| WO | WO 95/07662 | | 3/1995 |
| WO | WO 95/15124 | | 6/1995 |
| WO | WO 96/05776 | | 2/1996 |
| WO | WO 96/22056 | | 7/1996 |
| WO | WO 96/13218 | | 9/1996 |
| WO | WO 97/00646 | | 1/1997 |
| WO | WO 97/00647 | | 1/1997 |
| WO | WO 97/10764 | | 3/1997 |
| WO | WO 97/24073 | | 7/1997 |
| WO | WO 97/24993 | | 7/1997 |
| WO | WO 98/27880 | | 7/1998 |
| WO | WO 99/03407 | | 1/1999 |
| WO | WO 99/03408 | | 1/1999 |
| WO | WO 99/03409 | | 1/1999 |
| WO | WO 99/12488 | | 3/1999 |
| WO | WO 99/23933 | | 5/1999 |
| WO | WO 99/40857 | | 8/1999 |
| WO | WO 99/40861 | | 8/1999 |
| WO | WO 99/51158 | | 10/1999 |
| WO | WO 99/66850 | | 12/1999 |
| WO | WO 00/24330 | | 5/2000 |
| WO | WO 00/24331 | | 5/2000 |
| WO | WO 00/36986 | | 6/2000 |
| WO | WO 00/41638 | | 7/2000 |
| WO | WO 00/47124 | | 8/2000 |
| WO | WO 00/53112 | | 9/2000 |
| WO | WO 01/17448 | | 3/2001 |
| WO | WO 01/54604 | | 8/2001 |
| WO | WO 02/07627 | | 1/2002 |
| WO | WO 02/067798 | | 9/2002 |
| WO | WO 02/080783 | | 10/2002 |
| WO | WO 02/080784 | | 10/2002 |
| WO | WO 02/080785 | | 10/2002 |
| WO | WO 02/080786 | | 10/2002 |
| WO | WO 02/080793 | | 10/2002 |
| WO | WO 02/080794 | | 10/2002 |
| WO | WO 02/080795 | | 10/2002 |
| WO | WO 02/080796 | | 10/2002 |
| WO | WO 02/080797 | | 10/2002 |
| WO | WO 02/080798 | | 10/2002 |
| WO | WO 02/080799 | | 10/2002 |
| WO | WO 02/081170 | | 10/2002 |
| WO | WO 03/061500 | | 7/2003 |
| WO | WO 03/090630 | | 11/2003 |
| WO | WO 03/101311 | | 12/2003 |
| WO | WO 2004/032776 | | 4/2004 |
| WO | WO 2004/032777 | | 4/2004 |
| WO | WO 2004/052221 | | 6/2004 |
| WO | WO 2004/073488 | | 9/2004 |
| WO | WO 2004/073490 | | 9/2004 |
| WO | WO 2004/073753 | | 9/2004 |
| WO | WO 2004/082495 | | 9/2004 |
| WO | WO 2004/098383 | | 11/2004 |
| WO | WO 2004/103156 | | 12/2004 |
| WO | WO 2005/004734 | | 1/2005 |
| WO | WO 2005/004735 | | 1/2005 |
| WO | WO 2005/110264 | | 11/2005 |
| WO | WO 2008/045348 | | 4/2008 |
| WO | WO 2008/045350 | | 4/2008 |

OTHER PUBLICATIONS

Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 • dated Oct. 5, 2004.
Int'l Search Report PCT/US04/13273 dated Nov. 22, 2004.
Int'l Search Report PCT/US04/15311 dated Nov. 18, 2004.

* cited by examiner

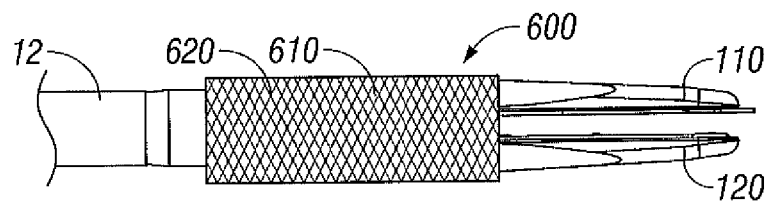
FIG. 5
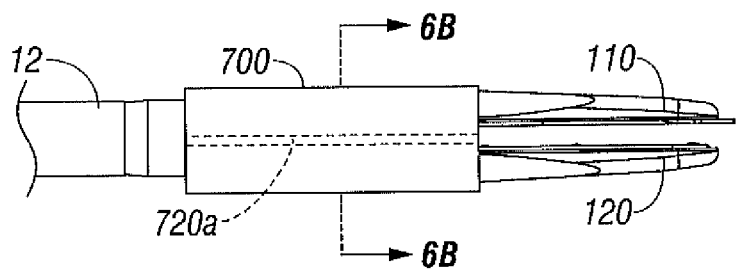 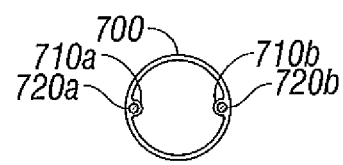
FIG. 6A  FIG. 6B
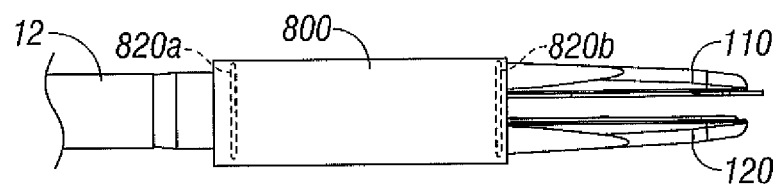
FIG. 7

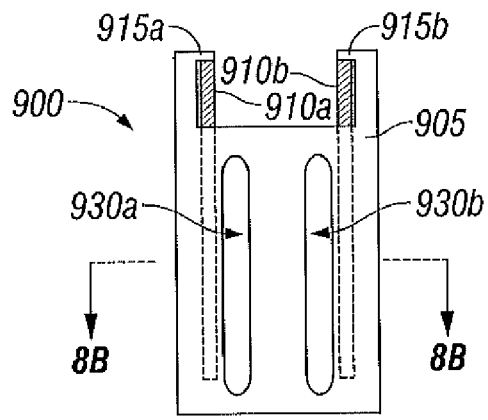
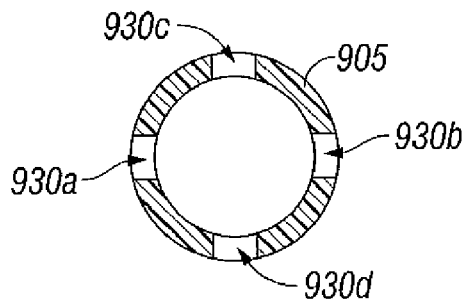
FIG. 8A     FIG. 8B
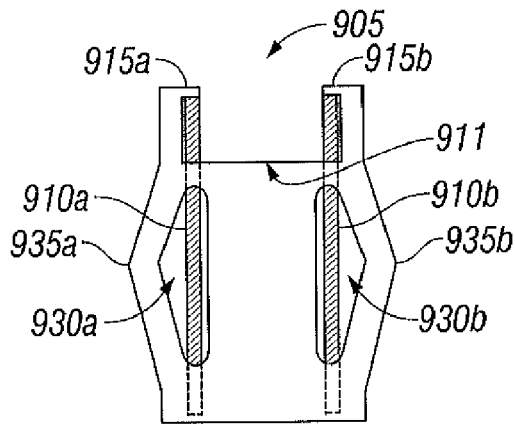
FIG. 8C
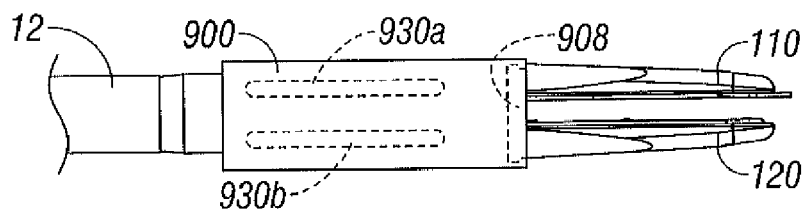
FIG. 8D
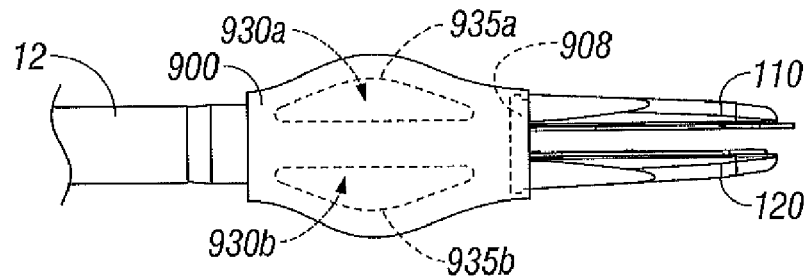
FIG. 8E

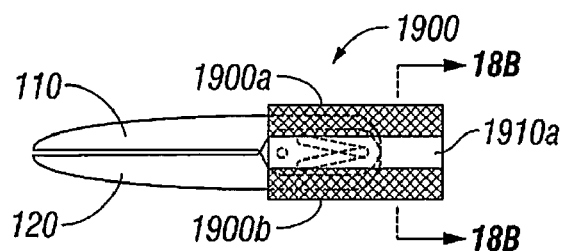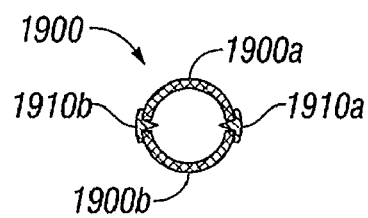
FIG. 18A    FIG. 18B
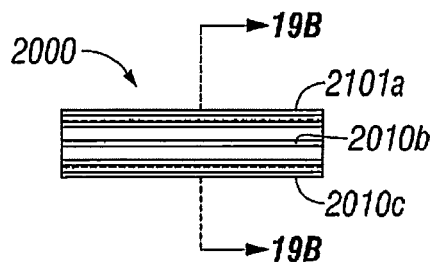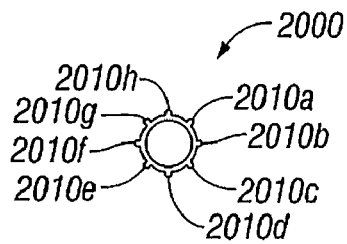
FIG. 19A    FIG. 19B
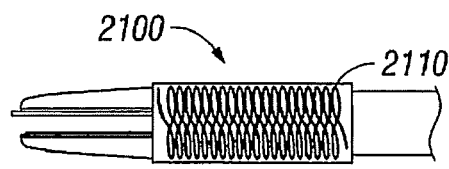
FIG. 20
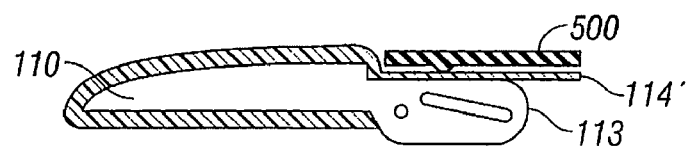
FIG. 21

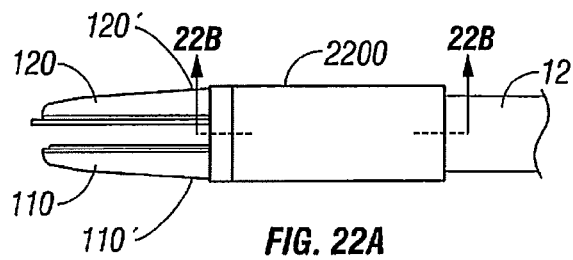 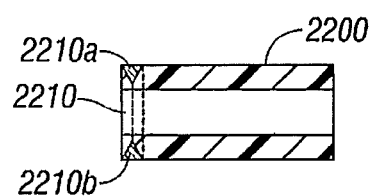
FIG. 22A  FIG. 22B
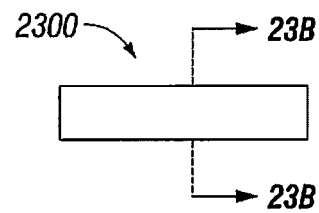 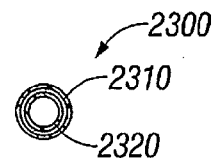
FIG. 23A  FIG. 23B
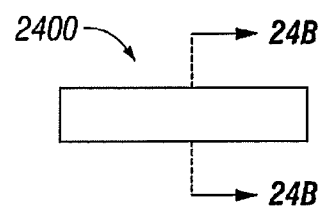 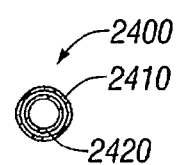
FIG. 24A  FIG. 24B
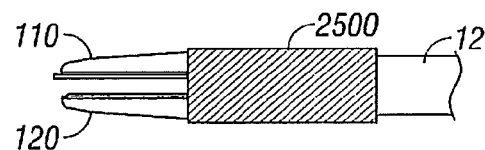
FIG. 25

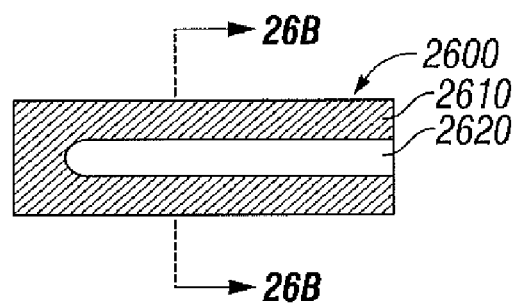
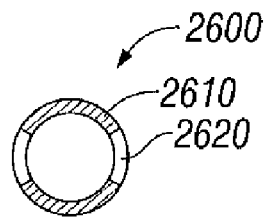
FIG. 26A  FIG. 26B
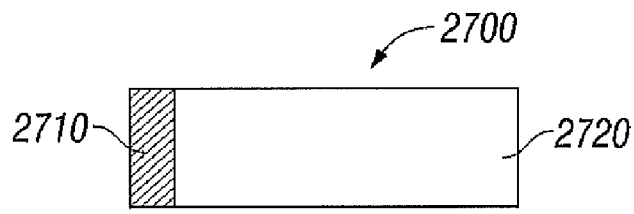
FIG. 27
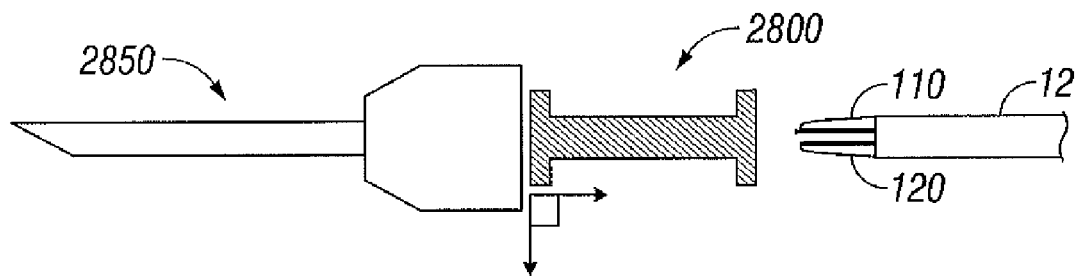
FIG. 28
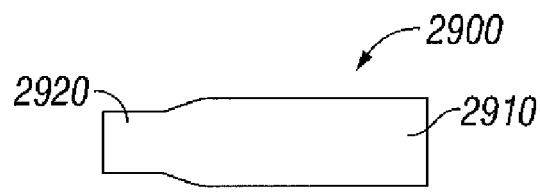
FIG. 29A

INSULATING SHEATH FOR ELECTROSURGICAL FORCEPS

CROSS REFERENCE TO RELATED APPLICATION

The present application claims the benefit of priority to U.S. Provisional Application Ser. No. 60/995,866 filed on Sep. 28, 2007, the entire contents of which is incorporated by reference herein.

BACKGROUND

1. Technical Field

The present disclosure relates to an insulated electrosurgical forceps and more particularly, the present disclosure relates to an insulating boot for use with either an endoscopic or open bipolar and/or monopolar electrosurgical forceps for sealing, cutting, and/or coagulating tissue.

2. Background of Related Art

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

A general issue with existing electrosurgical forceps is that the jaw members rotate about a common pivot at the distal end of a metal or otherwise conductive shaft such that there is potential for both the jaws, a portion of the shaft, and the related mechanism components to conduct electrosurgical energy (either monopolar or as part of a bipolar path) to the patient tissue. Existing electrosurgical instruments with jaws either cover the pivot elements with an inflexible shrink-tube or do not cover the pivot elements and connection areas and leave these portions exposed.

SUMMARY

The present disclosure relates to an electrosurgical forceps that includes a shaft having a pair of jaw members at a distal end thereof that are movable about a pivot from a first position wherein the jaw members are disposed in spaced relation relative to one another to a second position wherein the jaw members are closer to one another for grasping tissue. A movable handle is included that actuates a drive assembly to move the jaw members relative to one another and one or both of the jaw members are adapted to connect to a source of electrical energy such that the jaw members are capable of conducting energy to tissue held therebetween. An insulative sheath is fitted for removal atop at least a portion of an exterior surface of one or both jaw members, about the pivot and the distal end of the shaft. The insulative sheath houses a silicone lube configured to facilitate insertion of the forceps through a cannula after removal of the insulative sheath.

The present disclosure also relates to a method of facilitating insertion of a forceps through a cannula comprising the initial step of providing a forceps including: a shaft having a pair of jaw members at a distal end thereof that are movable about a pivot from a first position wherein the jaw members are disposed in spaced relation relative to one another to a second position wherein the jaw members are closer to one another for grasping tissue; one or both of the jaw members are adapted to connect to a source of electrical energy such that the jaw members are capable of conducting energy to tissue held therebetween; and an insulative sheath disposed atop at least a portion of an exterior surface of one or both jaw members, about the pivot and the distal end of the shaft, the insulative sheath housing a silicone lube configured to facilitate insertion of the forceps through a cannula after removal of the insulative sheath.

The method also includes the steps of: removing the insulative sheath to expose the silicone lube atop the exterior surface of the jaw member(s), about the pivot and the distal end of the shaft; engaging the forceps for insertion through a cannula; and inserting the forceps through the cannula utilizing the silicone lube to facilitate insertion.

BRIEF DESCRIPTION OF THE DRAWINGS

Various embodiments of the subject instrument are described herein with reference to the drawings wherein.

Figure 1:
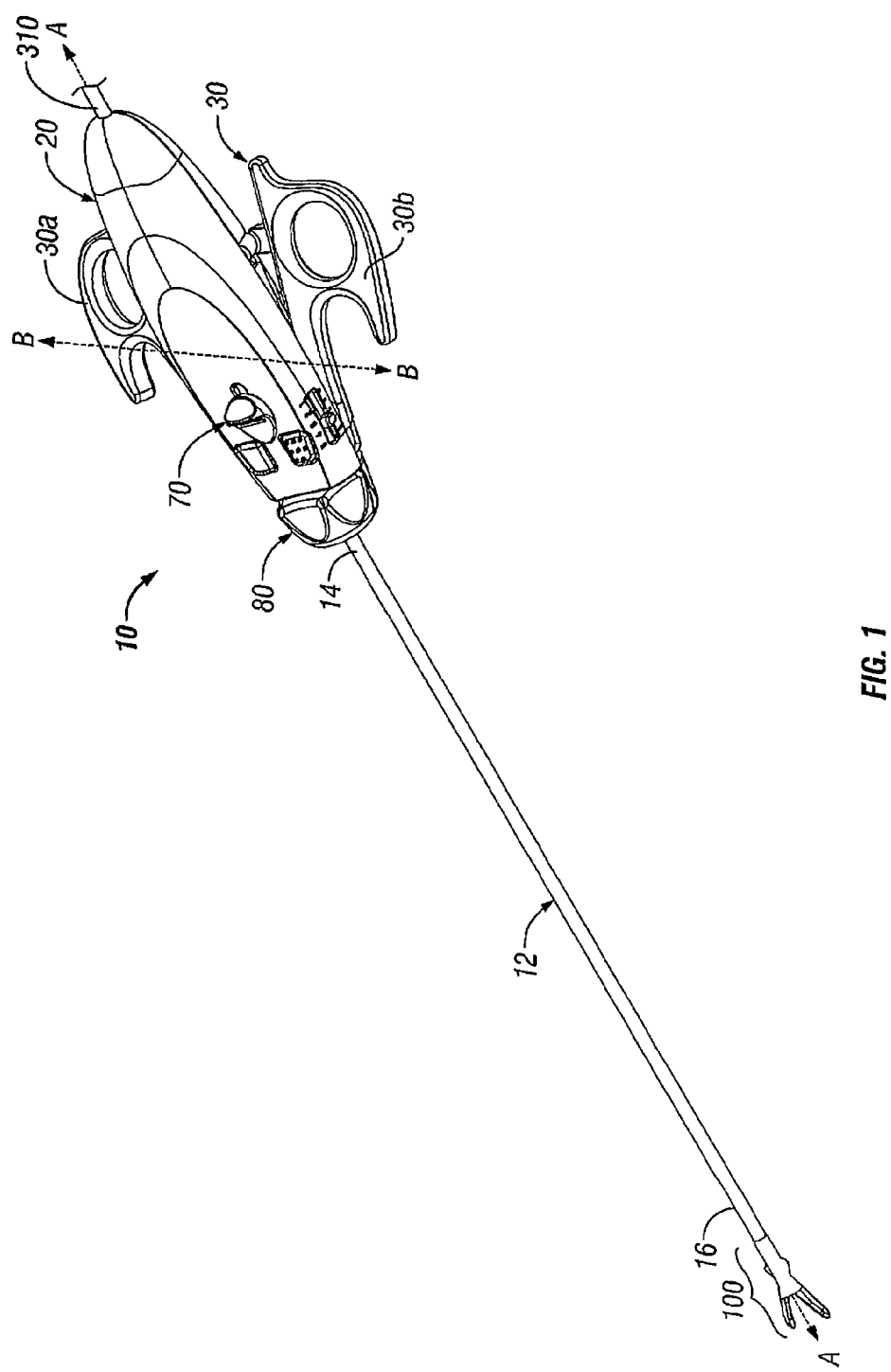
FIG. 1 is a left, perspective view including an endoscopic bipolar forceps showing a housing, a shaft and an end effector assembly having an insulating boot according to one embodiment of the present disclosure.
Figure 4A:
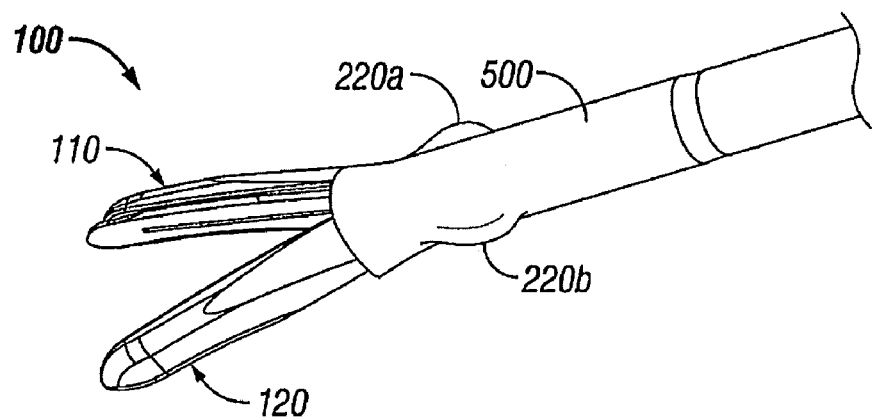
Figure 4B:
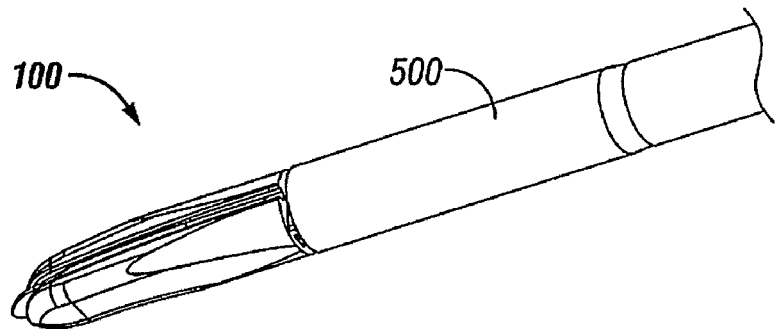
Figure 4C:
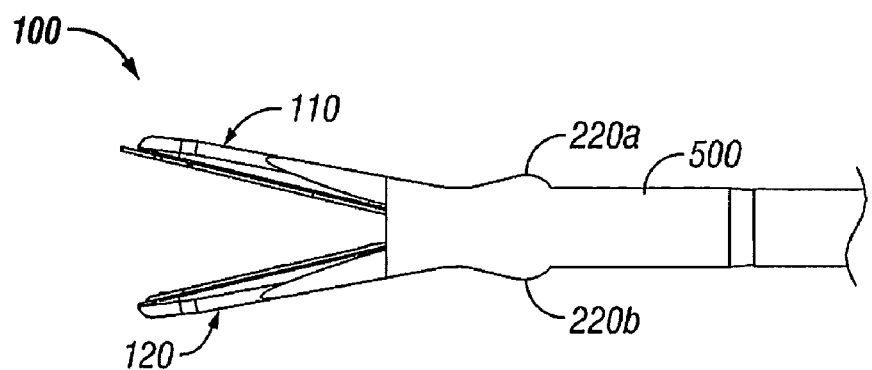

FIG. 4A is an rear perspective view of the end effector assembly of FIG. 1 showing a pair of opposing jaw members in an open configuration;

FIG. 4B is an rear perspective view of the end effector assembly of FIG. 1 showing a pair of opposing jaw members in a closed configuration;

FIG. 4C is an side view of the end effector assembly of FIG. 1 showing the jaw members in a open configuration;

FIG. 5 is an enlarged, schematic side view of the end effector assembly showing one embodiment of the insulating boot configured as a mesh-like material;

FIG. 6A is an enlarged, schematic side view of the end effector assembly showing another embodiment of the insulating boot which includes an enforcement wire disposed longitudinally therealong which is dimensioned to strengthen the boot;

FIG. 6B is a front cross section along line 6B-6B of FIG. 6A;

FIG. 7 is an enlarged, schematic side view of the end effector assembly showing another embodiment of the insulating boot which includes wire reinforcing rings disposed at the distal end proximal ends thereof;

FIG. 8A is an enlarged view of a another embodiment of the insulating boot according to the present disclosure;

FIG. 8B is a front cross section along line 8B-8B of FIG. 8A

Figure 9A:
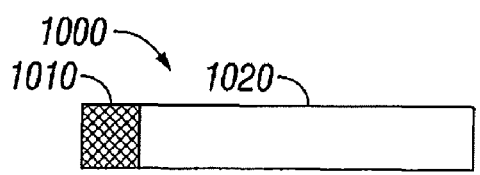
Figure 9B:
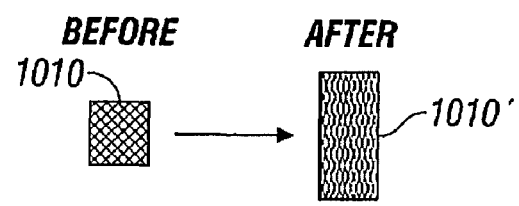
Figure 10:
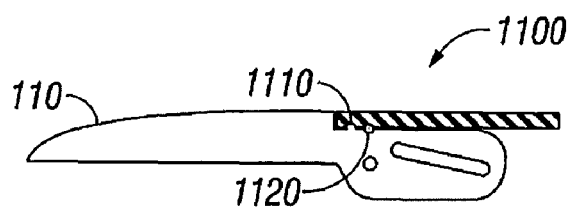
Figure 11:
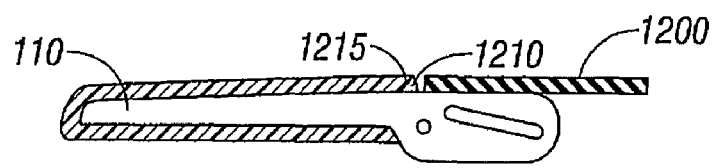
Figure 12:
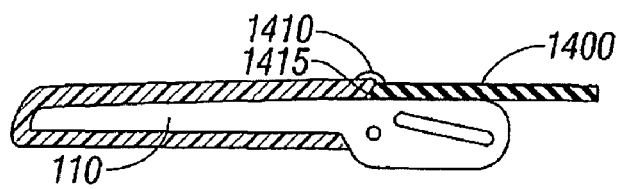
Figure 13:
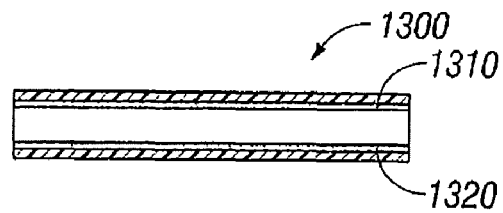
Figure 14:
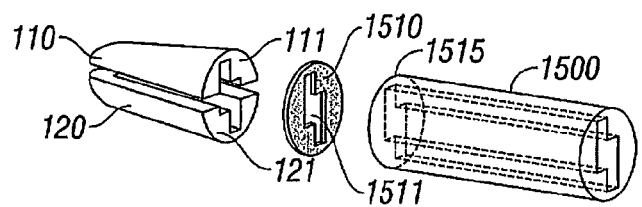
Figure 15A:
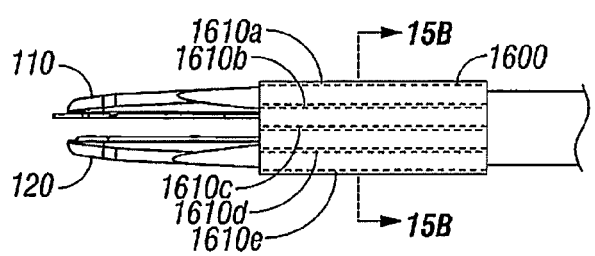
Figure 15B:
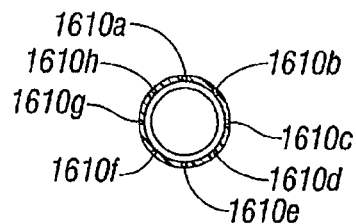
Figure 16:
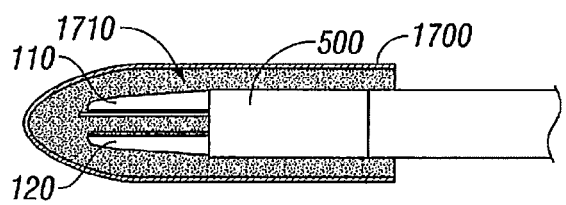
Figure 17A:
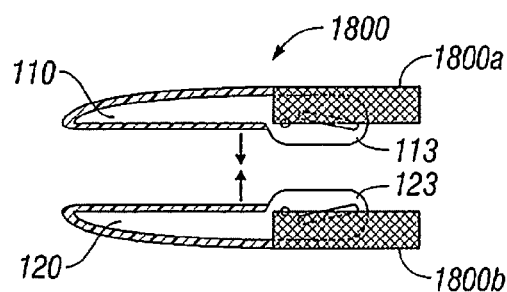
Figure 17B:
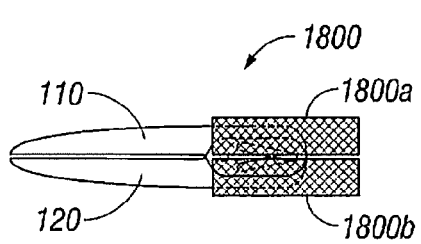
Figure 30:
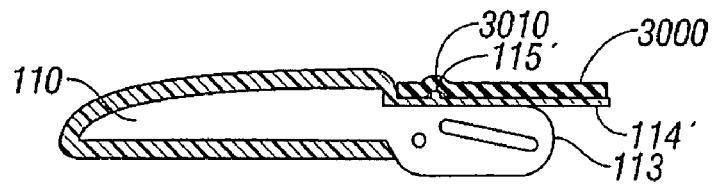
Figure 31:
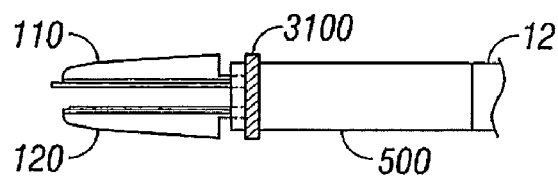
Figure 32:
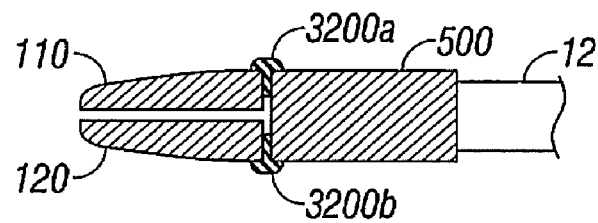
Figure 33A:
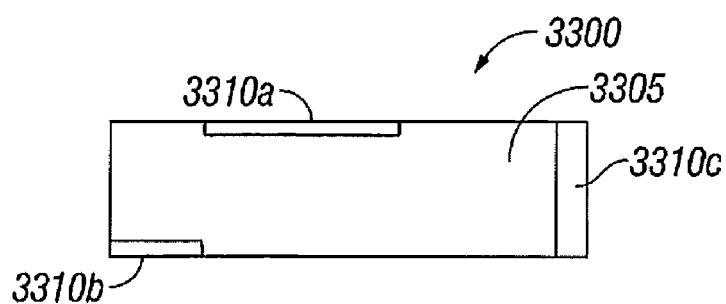
Figure 33B:
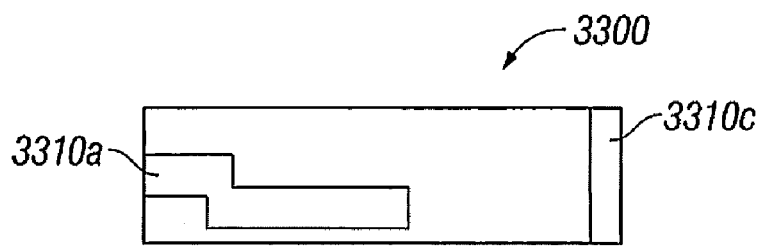
Figure 34:
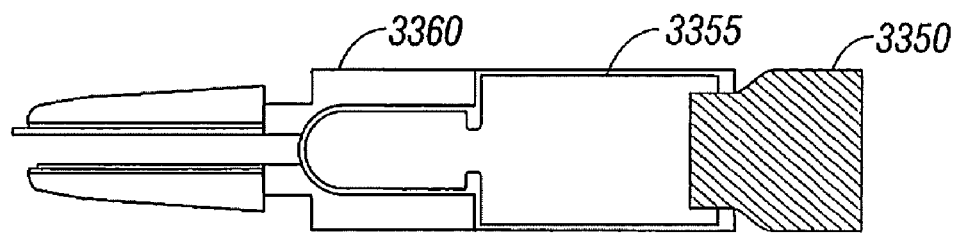
Figure 35A:
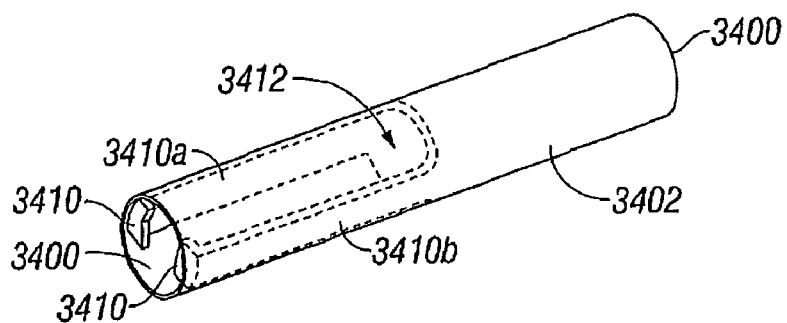
Figure 35B:
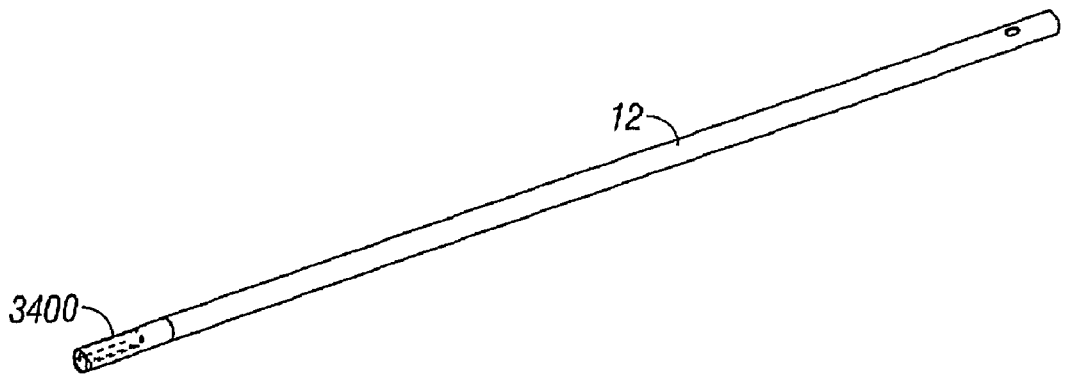

FIG. 8C is an enlarged view of the insulating boot of FIG. 8A shown in a partially compressed orientation;

FIG. 8D is an enlarged side view of the end effector assembly shown with the insulating boot of FIG. 8A disposed thereon;

FIG. 8E is an enlarged side view of the end effector assembly shown with the insulating boot of FIG. 8A disposed thereon shown in a partially compressed orientation;

FIG. 9A is an enlarged view of another embodiment of the insulating boot according to the present disclosure including a mesh and silicone combination;

FIG. 9B is a greatly-enlarged, broken view showing the radial expansion of the mesh portion of the insulating boot of FIG. 9A when longitudinally compressed;

FIG. 10 is an enlarged view of another embodiment of the insulating boot according to the present disclosure including a detent and dollop of adhesive to provide mechanical retention of the insulating boot atop the forceps jaws;

FIG. 11 is an enlarged view of another embodiment of the insulating boot according to the present disclosure including a chamfer section which provides an inflow channel for the adhesive during curing;

FIG. 12 is an enlarged view of another embodiment of the insulating boot according to the present disclosure including a heat activate adhesive flow ring which facilitates adherence of the insulating boot to the jaw members;

FIG. 13 is an enlarged view of another embodiment of the insulating boot according to the present disclosure including an adhesive layer which seals the junction between the insulating boot and the jaw overmold;

FIG. 14 is an enlarged view of another embodiment of the insulating boot according to the present disclosure which includes a tape layer to hold the boot against the back of the jaw members;

FIG. 15A is an enlarged view of another embodiment of the insulating boot according to the present disclosure including a ring of elastomer connections which both transfer current and facilitate retention of the insulating boot atop the jaw members;

FIG. 15B is a front cross section along line 15B-15B of FIG. 15A;

FIG. 16 is an enlarged view of another embodiment of the present disclosure which includes an insulating sheath filled with silicone gel to facilitate insertion of the cannula within a body cavity;

FIG. 17A is an enlarged view of another embodiment of the present disclosure which includes a plastic shield overmolded atop the jaw members to insulate the jaw members from one another;

FIG. 17B is an enlarged view of a the two jaw members of FIG. 17A shown assembled;

FIG. 18A is an enlarged view of another embodiment of the present disclosure similar to FIGS. 17A and 17B wherein a weather stripping is utilized to seal the gap between jaw members when assembled;

FIG. 18B is a front cross section along line 18B-18B of FIG. 18A;

FIG. 19A is an enlarged view of another embodiment of the present disclosure which includes an insulating boot with a series of radially extending ribs disposed therearound to reduce surface friction of the insulating boot during insertion through a cannula;

FIG. 19B is a front cross section along line 19B-19B of FIG. 19A;

FIG. 20 is an enlarged view of another embodiment of the present disclosure wherein a soft, putty-like material acts as the insulator for the various moving parts of the jaw members;

FIG. 21 is an enlarged view of another embodiment of the present disclosure which includes an insulating shield disposed between the boot and the metal sections of the jaw members;

FIG. 22A is an enlarged view of another embodiment of the present disclosure which includes a plastic wedge disposed between the boot and the proximal end of the jaw members which allows the jaw members to pivot;

FIG. 22B is a cross section along line 22B-22B of FIG. 22A;

FIG. 23A is an enlarged view of another embodiment of the present disclosure which includes a silicone boot with a ring disposed therein which is composed of an adhesive material which actively fills any holes created by arcing high current discharges;

FIG. 23B is a cross section along line 23B-23B of FIG. 23A;

FIG. 24A is an enlarged view of another embodiment of the present disclosure which includes a silicone boot with an ring disposed therein which is composed of an insulative material which actively fills any holes created by arcing high current discharges;

FIG. 24B is a cross section along line 24B-24B of FIG. 24A;

FIG. 25 is an enlarged view of another embodiment of the present disclosure wherein a distal end of a shaft which is overmolded with a silicone material;

FIG. 26A is an enlarged view of another embodiment of the present disclosure which includes an insulating boot being made from a low durometer material and a high durometer material—the low durometer material being disposed about the moving parts of the jaw members;

FIG. 26B is a cross section along line 26B-26B of FIG. 26A;

FIG. 27 is an enlarged view of another embodiment of the present disclosure which includes an insulating ring being made from a high durometer material;

FIG. 28 is an enlarged view of another embodiment of the present disclosure which includes an insulating boot which is packaged with a cannula and designed for engagement over the jaw members when the jaw members are inserted into the cannula;

FIGS. 29A-29D are enlarged views of other embodiments of the present disclosure which includes an insulating boot having varying inner and outer diameters;

FIG. 30 is an enlarged view of another embodiment of the present disclosure which includes an insulating boot having a detent in the jaw overmold which is designed to mechanically engage the insulating boot;

FIG. 31 is an enlarged view of another embodiment of the present disclosure which includes an insulating boot having a tapered distal end;

FIG. 32 is an enlarged view of another embodiment of the present disclosure which includes an insulating boot having a square taper distal end;

FIGS. 33A and 33B are enlarged views of another embodiment of the present disclosure which includes a co-molded boot having a silicone portion and proximal and side portions made a thermoplastic material;

FIG. 34 is an enlarged view of another embodiment having a silicone boot with a plastic shell overlapped with a heat shrink tubing;

FIG. 35 is an enlarged view of another embodiment of the present disclosure which includes a weather strip type mechanical interface disposed at the junction of the boot and the jaw members;

FIGS. 35A-35B is an enlarged view of another embodiment of the present disclosure including a thermoplastic clevis having a pair of fingers and which project inwardly to mechanically engage the proximal end of jaw members.

Figure 36:
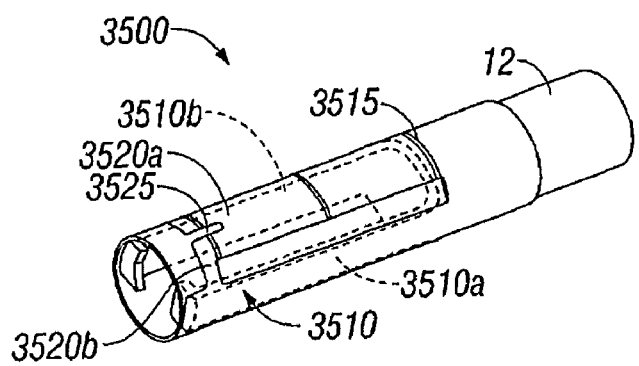
Figure 37:
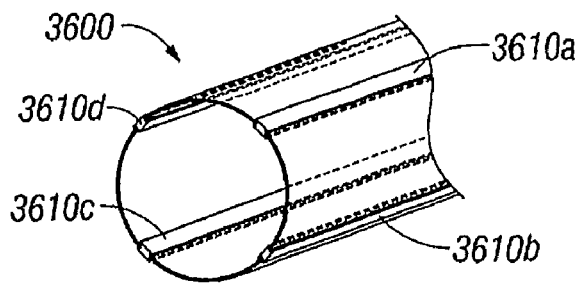
Figure 38A:
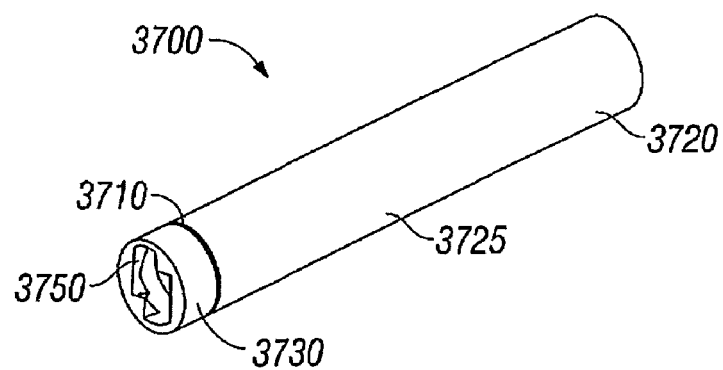
Figure 38B:
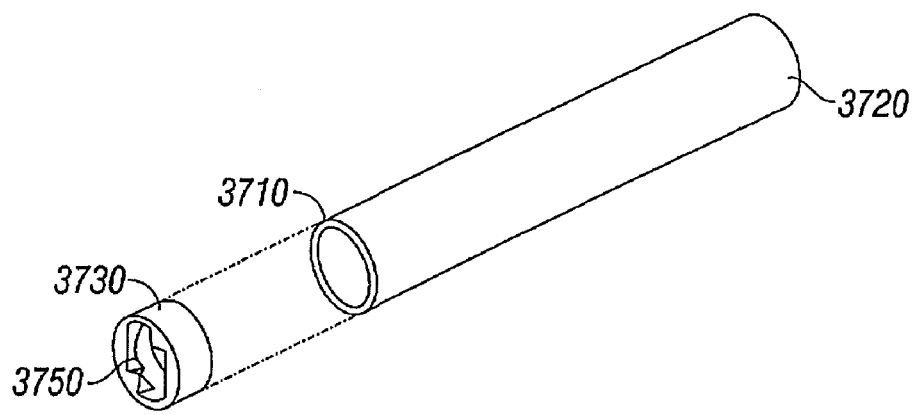
Figure 38C:
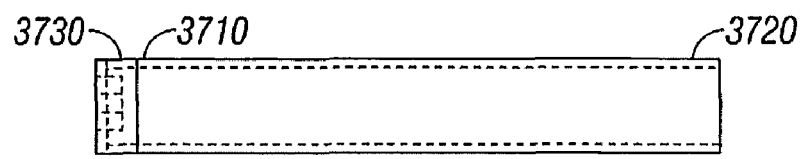
Figure 38D:
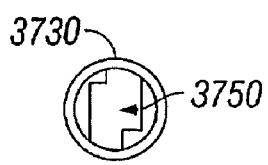
Figure 39A:
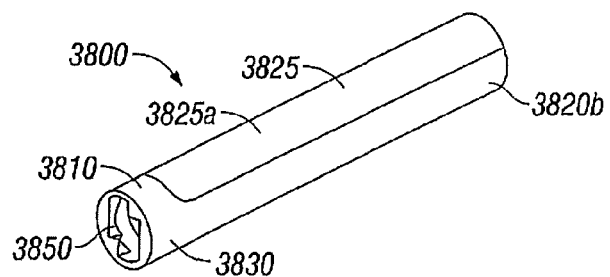
Figure 39B:
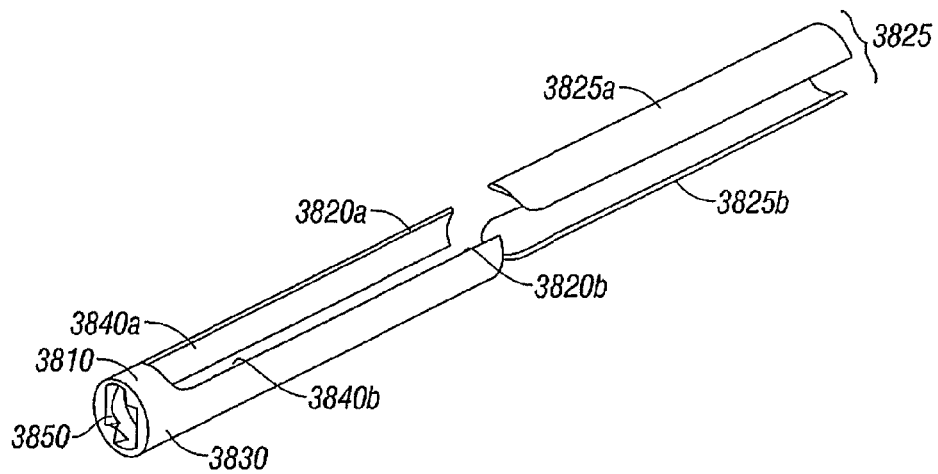
Figure 39C:
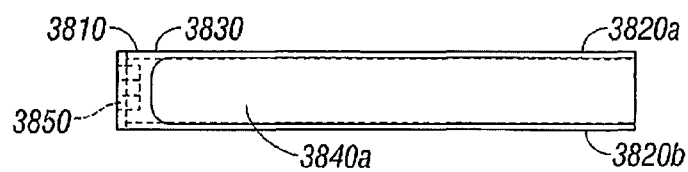
Figure 39D:
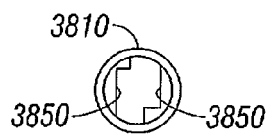
Figure 40:
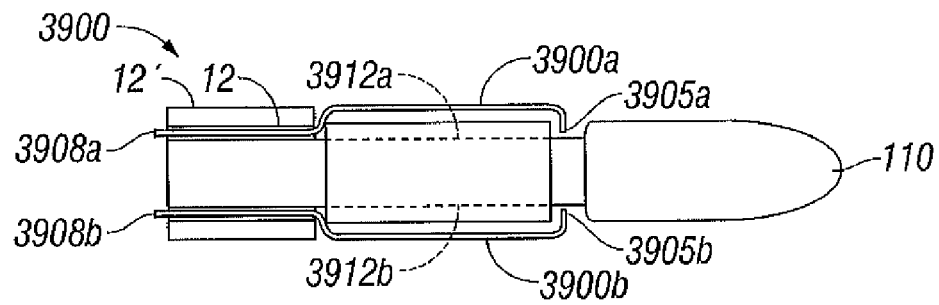
Figure 41:
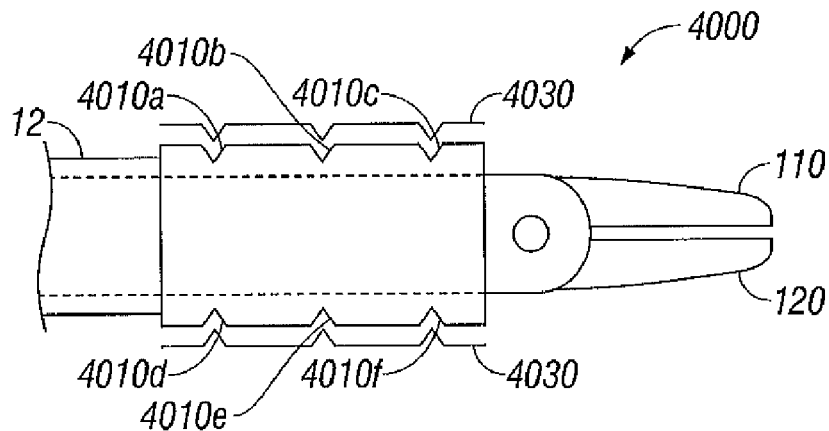
Figure 42:
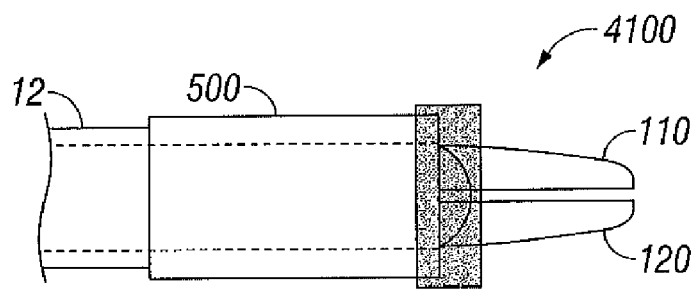
Figure 43:
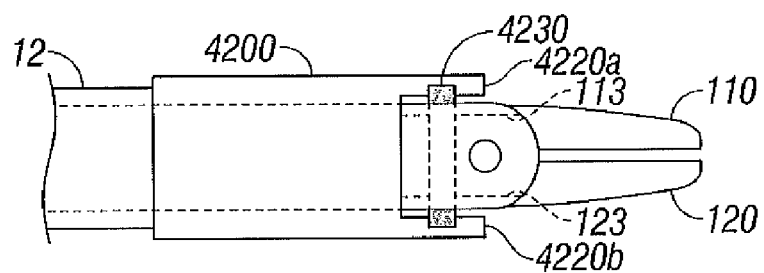
Figure 44A:
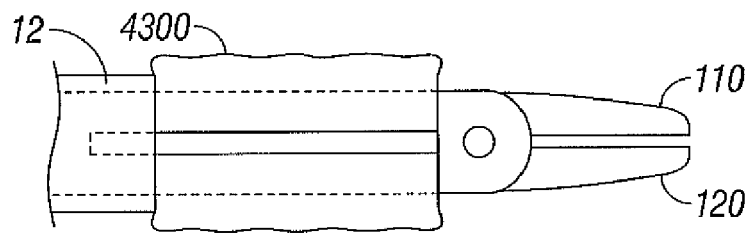
Figure 44B:
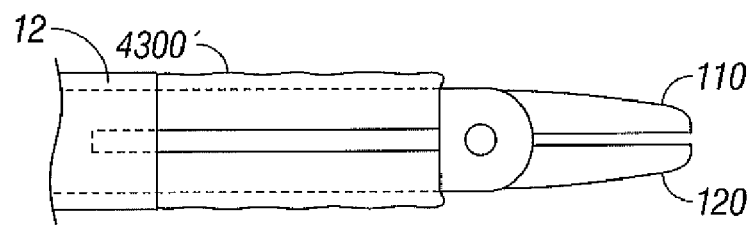
Figure 45A:
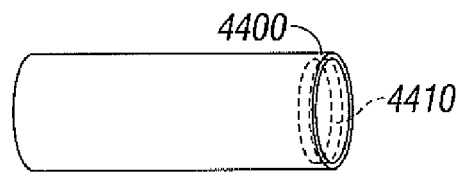
Figure 45B:
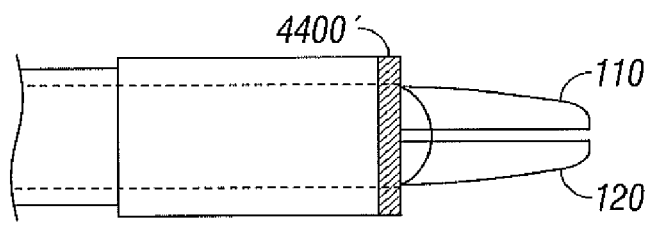
Figure 46:
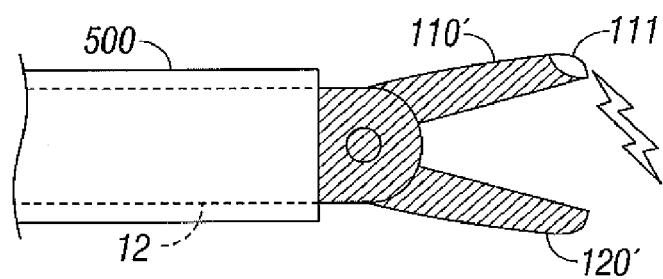

FIG. 36 is an enlarged view of another embodiment of the present disclosure which includes a silicone overmolded clevis similar to the embodiment of FIG. 38 which also includes a thermoplastic tube configured to encompass an endoscopic shaft member FIG. 37 is an enlarged view of another embodiment of the present disclosure with thermoplastic rails along a length thereof;

FIG. 38A-38D are enlarged views of another embodiment of the present disclosure which includes an insulating boot with a ring-like mechanical interface which is configured to include a key-like interface for engaging the proximal ends of the jaw members;

FIG. 39A-39D are enlarged views of another embodiment of the present disclosure which includes an insulating boot having a key-like interface disposed at a distal end thereof for engaging the proximal ends of the jaw members, the insulating boot being made from a low durometer material and a high durometer material;

FIG. 40 are enlarged views of another embodiment of the present disclosure which includes a plastic guard rail which secures the insulating boot to the jaw members and heat shrink material by a series of hook-like appendages;

FIG. 41 is an enlarged view of another embodiment of the present disclosure which includes an insulating boot having a series of pores defined in an outer periphery thereof, the pores having a heat activated lubricant disposed therein the facilitate insertion of the forceps within a cannula;

FIG. 42 is an enlarged view of another embodiment of the present disclosure which includes a heat-cured adhesive which is configured to mechanically engage and secure the insulating boot to the jaw members;

FIG. 43 is an enlarged view of another embodiment of the present disclosure which includes an insulating boot having an overlapping portion which engages overlaps the jaw members, the jaw members including a hole defined therein which contains a glue which bonds to the overlapping portion of the insulating boot;

FIGS. 44A-44B are enlarged views of another embodiment of the present disclosure which includes an uncured adhesive sleeve which is configured to engage the distal end of the shaft and the jaw members and bond to the uninsulated parts when heated;

FIGS. 45A-45B are enlarged views of another embodiment of the present disclosure which includes an insulating boot having an uncured adhesive ring which is configured to bond and secure the insulating boot to the jaw members when heated; and FIG. 46 is an enlarged view of another embodiment of the present disclosure which includes a coating disposed on the exposed portions of the jaw members, the coating being made from a material that increases resistance with heat or current.

DETAILED DESCRIPTION

Figure 2A:
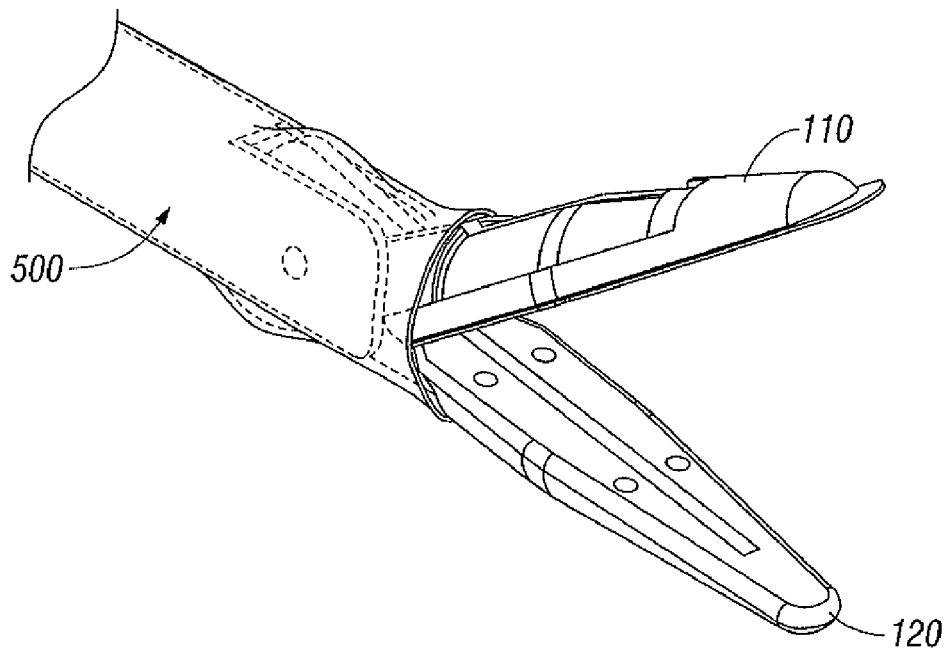
FIG. 2A is an enlarged, right perspective view of the end effector assembly with a pair of jaw members of the end effector assembly shown in open configuration having the insulating boot according to the present disclosure.
Figure 2B:
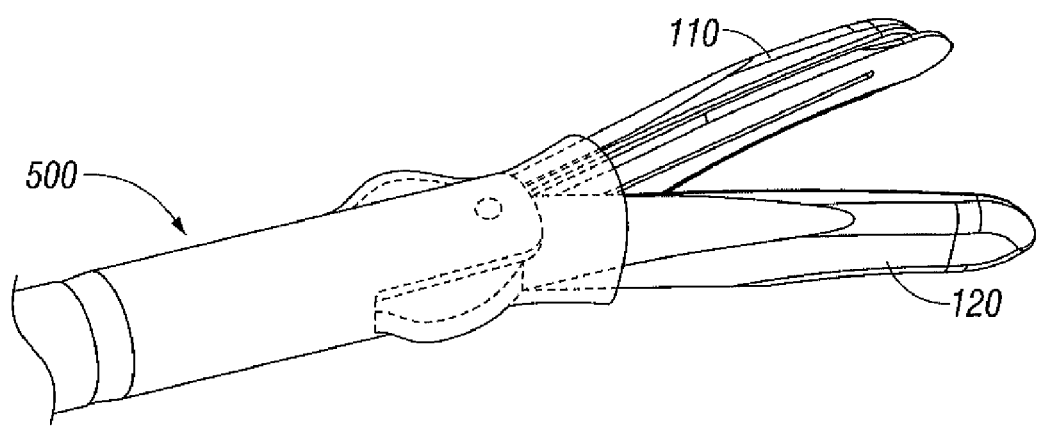
FIG. 2B is an enlarged, bottom perspective view of the end effector assembly with the jaw members shown in open configuration having the insulating boot according to the present disclosure.

Referring initially to FIGS. 1-2B, one particularly useful endoscopic forceps 10 is shown for use with various surgical procedures and generally includes a housing 20, a handle assembly 30, a rotating assembly 80, a trigger assembly 70 and an end effector vascular tissue. For the purposes herein, forceps 10 will be described generally. However, the various particular aspects of this particular forceps are detailed in commonly owned U.S. patent application Ser. No. 10/460, 926, now U.S. Pat. No. 7,156,846 B2, "VESSEL SEALER AND DIVIDER FOR USE WITH SMALL TROCARS AND CANNULAS", issued to Dycus et al. on Jan. 2, 2007, U.S. patent application Ser. No. 10/953,757, now U.S. Pat. No. 7,150,749 B2, "VESSEL SEALER AND DIVIDER HAVING ELONGATED KNIFE STROKE AND SAFETY CUTTING MECHANISM", issued to Dycus et al. on Dec. 19, 2006, and U.S. patent application Ser. No. 11/348,072, now U.S. Pat. No. 7,771,425 B2, "VESSEL SEALER AND DIVIDER HAVING A VARIABLE JAW CLAMPING MECHANISM", issued to Dycus et al. on Aug. 10, 2010, the entire contents of all of which are incorporated by reference herein.

Forceps 10 also includes a shaft 12 that has a distal end 16 dimensioned to mechanically engage the end effector assembly 100 and a proximal end 14 that mechanically engages the housing 20 through rotating assembly 80. As will be discussed in more detail below, the end effector assembly 100 includes a flexible insulating boot 500 configured to cover at least a portion of the exterior surfaces of the end effector assembly 100.

Forceps 10 also includes an electrosurgical cable 310 that connects the forceps 10 to a source of electrosurgical energy, e.g., a generator (not shown). The generator includes various safety and performance features including isolated output, independent activation of accessories, and Instant Response™ technology (a proprietary technology of Valleyiab, Inc., a division of Tyco Healthcare, LP) that provides an advanced feedback system to sense changes in tissue many times per second and adjust voltage and current to maintain appropriate power. Cable 310 is internally divided into a series of cable leads (not shown) that each transmit electrosurgical energy through their respective feed paths through the forceps 10 to the end effector assembly 100.

Handle assembly 30 includes a two opposing handles 30a and 30b which are each movable relative to housing 20 from a first spaced apart position wherein the end effector is disposed in an open position to a second position closer to housing 20 wherein the end effector assembly 100 is positioned to engage tissue. Rotating assembly 80 is operatively associated with the housing 20 and is rotatable in either direction about a longitudinal axis "A" (See FIG. 1). Details of the handle assembly 30 and rotating assembly 80 are described in the above-referenced patent applications, namely, U.S. patent application Ser. No. 10/460,926, now U.S. Pat. No. 7,156,846 B2, U.S. patent application Ser. No. 10/953,757, now U.S. Pat. No. 7,150,749 B2, and U.S. patent application Ser. No. 11/348,072, now U.S. Pat. No. 7,771,425 B2.

As mentioned above and as shown best in FIGS. 2A and 2B, end effector assembly 100 is attached at the distal end 14 of shaft 12 and includes a pair of opposing jaw members 110 and 120. Opposing handles 30a and 30b of handle assembly 30 are ultimately connected to a drive assembly (not shown) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. All of these components and features are best explained in detail in the above-identified commonly owned U.S. application Ser. No. 10/460,926, now U.S. Pat. No. 7,156,846 B2.

Figure 3:
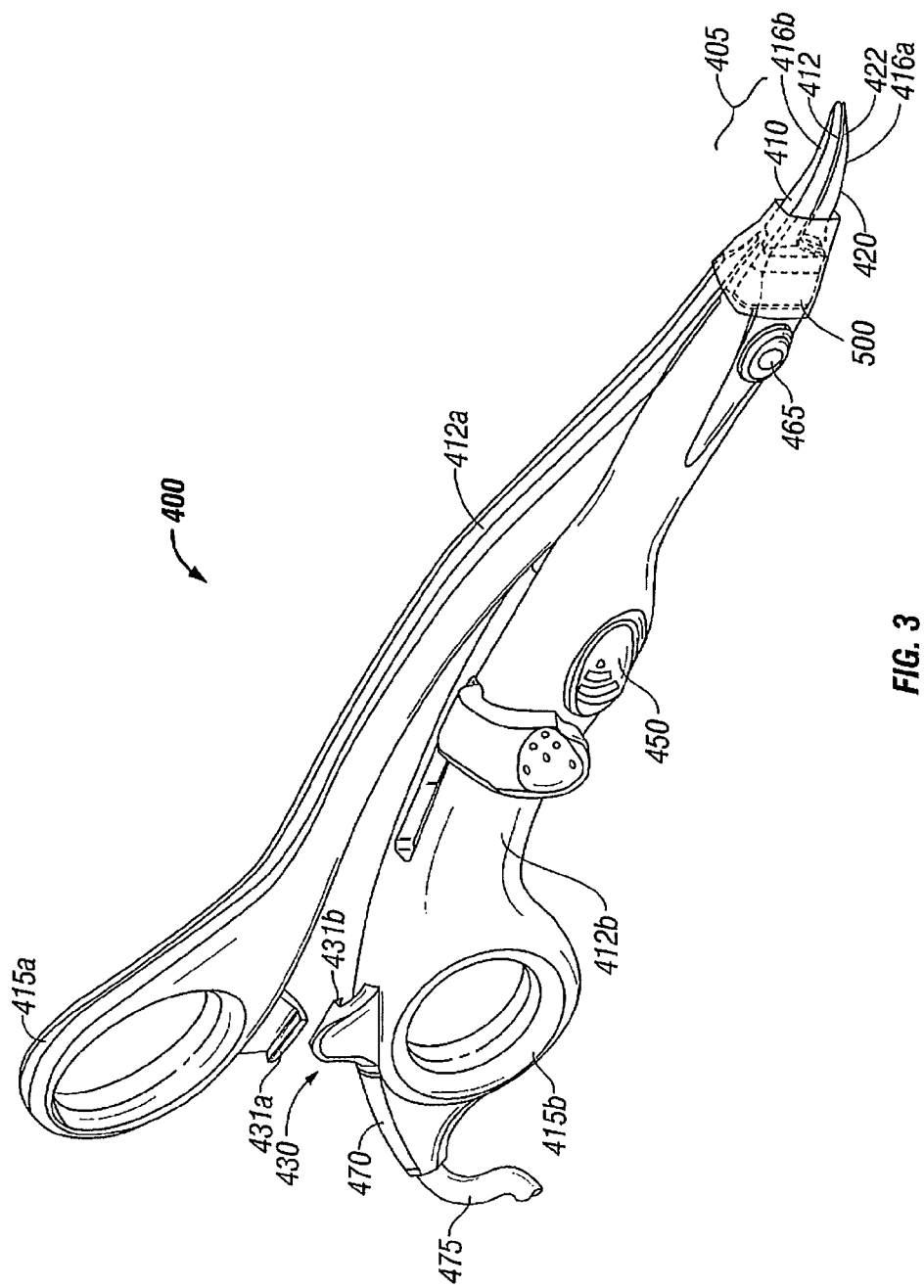
FIG. 3 is a right, perspective view of another version of the present disclosure that includes an open bipolar forceps_ showing a housing, a pair of shaft members and an end effector assembly having an insulating boot according to the present disclosure.

FIG. 3 shows insulating boot 500 configured to engage a forceps 400 used in open surgical procedures. Forceps 400 includes elongated shaft portions 412a and 412b having an end effector assembly 405 attached to the distal ends 416a and 416b of shafts 412a and 412b, respectively. The end effector assembly 405 includes pair of opposing jaw members 410 and 420 which are pivotably connected about a pivot pin 465 and which are movable relative to one another to grasp tissue.

Each shaft 412a and 412b includes a handle 415a and 415b, respectively, disposed at the proximal ends thereof. As can be appreciated, handles 415a and 415b facilitate movement of the shafts 412a and 412b relative to one another which, in turn, pivot the jaw members 410 and 420 from an open position wherein the jaw members 410 and 420 are disposed in spaced relation relative to one another to a clamping or closed position wherein the jaw members 410 and 420 cooperate to grasp tissue therebetween. Details relating to the internal mechanical and electromechanical components of forceps 400 are disclosed in commonly-owned U.S. patent application Ser. No. 10/962,116, now U.S. Pat. No. 7,811,283 B2, "OPEN VESSEL SEALING INSTRUMENT WITH HOURGLASS CUTTING MECHANISM AND OVER-RATCHET SAFETY", issued to Moses et al. on Oct. 12, 2010. As will be discussed in more detail below, an insulating boot 500 or other type of insulating device as described herein may be configured to cover at least a portion of the exterior surfaces of the end effector assembly 405 to reduce stray current concentrations during electrical activation.

As best illustrated in FIG. 3, one of the shafts, e.g., 412b, includes a proximal shaft connector 470 which is designed to connect the forceps 400 to a source of electrosurgical energy such as an electrosurgical generator (not shown). The proximal shaft connector 470 electromechanically engages an electrosurgical cable 475 such that the user may selectively apply electrosurgical energy as needed. The cable 470 connects to a handswitch 450 to permit the user to selectively apply electrosurgical energy as needed to seal tissue grasped between jaw members 410 and 420. Positioning the switch 450 on the forceps 400 gives the user more visual and tactile control over the application of electrosurgical energy. These aspects are explained below with respect to the discussion of the handswitch 450 and the electrical connections associated therewith in the above-mentioned commonly-owned U.S. patent application Ser. No. 10/962,116, now U.S. Pat. No. 7,811,283 B2.

A ratchet 430 is included which is configured to selectively lock the jaw members 410 and 420 relative to one another in at least one position during pivoting. A first ratchet interface 431a extends from the proximal end of shaft member 412a towards a second ratchet interface 431b on the proximal end of shaft 412b in general vertical registration therewith such that the inner facing surfaces of each ratchet 431a and 431b abut one another upon closure of the jaw members 410 and 420 about the tissue. The ratchet position associated with the cooperating ratchet interfaces 431a and 431b holds a specific, i.e., constant, strain energy in the shaft members 412a and 412b which, in turn, transmits a specific closing force to the jaw members 410 and 420.

The jaw members 410 and 420 are electrically isolated from one another such that electrosurgical energy can be effectively transferred through the tissue to form a tissue seal. Jaw members 410 and 420 both include a uniquely-designed electrosurgical cable path disposed therethrough which transmits electrosurgical energy to electrically conductive sealing surfaces 412 and 422, respectively, disposed on the inner facing surfaces of jaw members, 410 and 420.

Turning now to the remaining figures, FIGS. 4A-46, various envisioned embodiments of electrical insulating devices are shown for shielding, protecting or otherwise limiting or directing electrical currents during activation of the forceps 10, 400. More particularly, FIGS. 4A-4C show one embodiment wherein the proximal portions of the jaw members 110 and 120 and the distal end of shaft 12 are covered by the resilient insulating boot 500 to reduce stray current concentrations during electrosurgical activation especially in the monopolar activation mode. More particularly, the boot 500 is flexible from a first configuration (See FIG. 4B) when the jaw members 110 and 120 are disposed in a closed orientation to a second expanded configuration (See FIGS. 4B and 4C) when the jaw members 110 and 120 are opened. When the jaw members 110 and 120 open, the boot flexes or expands at areas 220a and 220b to accommodate the movement of a pair of proximal flanges 113 and 123 of jaw members 110 and 120, respectively (see FIGS. 17A and 17B). Further details relating to one envisioned insulating boot 500 are described with respect to commonly-owned U.S. application Ser. No. 11/529,798 entitled "INSULATING BOOT FOR ELECTROSURGICAL FORCEPS", now U.S. Pat. No. 7,846,161 B2 issued to Dumbauld et al. on Dec. 7, 2010, the entire contents of which being incorporated by reference herein.

FIG. 5 shows another embodiment of an insulating boot 600 which is configured to reduce stray current concentrations during electrical activation of the forceps 10. More particularly, the insulating boot 600 includes a woven mesh 620 which is positioned over a proximal end of the jaw members 110 and 120 and a distal end of the shaft 12. During manufacturing, the mesh 620 is coated with a flexible silicone-like material 610 which is designed to limit stray currents from emanating to surrounding tissue areas. The woven mesh 620 is configured to provide strength and form to the insulating boot 600. The woven mesh 620 is also configured to radially expand when the mesh 620 longitudinally contracts (See FIGS. 9A and 9B).

FIGS. 6A and 6B show another embodiment of an insulating boot 700 which includes a pair of longitudinally extending wires 720a and 720b encased within corresponding channels 710a and 710b, respectively, defined within the boot 700.

The wires 720a and 720b re-enforce the boot 700 and may be manufactured from conductive or non-conductive materials. As can be appreciated, any number of wires 720a and 720b may be utilized to support the insulating boot 700 and enhance the fit of the boot 700 atop the jaw members 110 and 120. The wires 720a and 720b may be adhered to an outer periphery of the boot 700, adhered to an inner periphery of the boot 700, recessed within one or more channels disposed in the outer or inner periphery of the boot 700 or co-extruded or insert-molded into the insulating boot 700. The wires 720a and 720b may be manufactured from a flexible metal, surgical stainless steel, NiTi, thermoplastic, polymer, high durometer material and combinations thereof.

FIG. 7 shows another embodiment of an insulating boot 800 which includes a pair of circumferential wires 820a and 820b disposed within or atop the boot 800. The wires 820a and 820b re-enforce the boot 700 at the proximal and distal ends thereof and may be manufactured from conductive or non-conductive materials such as flexible metals, surgical stainless steel, NiTi, thermoplastic and polymers. Due to the tensile strength of the wires 820a and 820b, the boot 800 stays in place upon insertion though a cannula and further prevents the boot 800 from rolling onto itself during repeated insertion and/or withdrawal from a cannula. As can be appreciated, any number of wires 820a and 820b may be utilized to support the insulating boot 800 and enhance the fit of the boot atop the jaw members 110 and 120. For example, in one embodiment, the wires are insert molded to the boot 800 during a manufacturing step.

FIGS. 8A-8E show yet another embodiment of an insulating boot 900 which includes a molded thermoplastic shell 905 having a series of slits 930a-930d disposed therethrough which are configured to flex generally outwardly (See FIGS. 8C and 8E) upon the travel of the forceps shaft 12 to actuate the jaw members 110 and 120 to the open configuration. Shell 905 includes an inner periphery thereof lined with a silicone-like material 910a and 910b which provides patient protection from electrosurgical currents during activation while outer thermoplastic shell 905 protects the silicone material 910a and 910b during insertion and retraction from a surgical cannula (not shown). The outer shell 905 and the silicone-like material 910a and 910b may be overmolded or co-extruded during assembly.

As mentioned above, the outer shell 905 expands at expansion points 935a and 935b upon contraction of the shaft 12 or movement of the jaw members 110 and 120. During expansion of the shell 905, the shell 905 does not adhere to the inner silicone material 910a and 910b due the inherent properties of the silicone material 910a and 910b and selective texturing thereof. Shell 905 may also include an inner rim or latching areas 915a and 915b disposed at the distal (and/or proximal) end thereof. The latching areas 915a and 915b are configured to mechanically interface with the jaw members 110 and 120 and hold the shell 905 in place during relative movement of the shaft 12. Other mechanical interfaces 908 may also be included which are configured to engage the shell 905 with the jaw members and/or shaft 12, e.g., adhesive. The outer shell 905 may include a relief section 911 to facilitate engagement of the outer shell 905 atop the jaw members 110 and 120.

FIGS. 9A and 9B show yet another embodiment of the insulating boot 1000 which is configured to include an insulative mesh 1010 disposed at one end of boot 1000 and a silicone (or the like) portion 1020 disposed at the other end thereof. Mesh portion 1010 is configured to radially expand and longitudinally contract from a first configuration 1010 to a second configuration 1010' as shown in FIG. 9B. The mesh portion 1010 is typically associated with the part of the boot closest to the jaw members 110 and 120.

FIG. 10 shows yet another embodiment of the insulating boot 1100 which is configured to mechanically engage a corresponding mechanical interface 1110 (e.g., detent or bump) disposed on a proximal end of the jaw members, e.g., jaw member 110. An adhesive 1120 may also be utilized to further mechanical retention. The at least one mechanical interface 1110 may also include a raised protuberance, flange, spike, cuff, rim, bevel and combinations thereof. The mechanical interface 1110 may be formed by any one of several known processes such as co-extrusion and overmolding.

Similarly, one or both jaw members 110 and 120 may include an underlapped or chamfered section 1215 which enhances mechanical engagement with the insulating boot 1200. For example and as best shown in FIG. 11, an adhesive 1210 may be utilized between the beveled section 1215 defined in jaw member 110 and the insulating boot 1200 to enhance mechanical engagement of the boot 1200. Further and as best shown in FIG. 12, an adhesive 1410 may be utilized to atop the intersection of the bevel 1415 and insulating boot 1400 to further mechanical retention of the boot 1400. The adhesive 1410 may be configured to cure upon application of heat, ultraviolet light, electrical energy or other ways customary in the trade.

FIG. 13 shows yet another embodiment of an insulating boot 1300 which includes an internally-disposed glue ring 1310 disposed along the inner periphery 1320 of the boot 1300. The glue ring 1310 is configured to cure when heated or treated with light (or other energy) depending upon a particular purpose or manufacturing sequence.

FIG. 14 shows yet another embodiment of an insulating boot 1500 which is configured to cooperate with a glue-like tape 1510 which holds the insulating boot 1500 in place atop the proximal ends 111 and 121 of the jaw members 110 and 120, respectively. Tape 1510 may be configured to cure upon application of heat or other energy. The tape 1510 may also be configured to include an aperture 1511 defined therein which is dimensioned to receive the proximal end of the jaw members 110 and 120.

FIGS. 15A and 15B show yet another embodiment of an insulating boot 1600 which includes a series of electrical leads 1610a-1610h disposed therethrough which are designed to electromechanically engage the jaw members 110 and 120 and supply current thereto. More particularly, boot 1600 may include leads 1610a-1610d which carry on electrical potential to jaw member 110 and leads 1610e-1610h which are designed to carry a second electrical potential to jaw member 120. The leads 1610a-1610h may be configured as metal strands disposed along the inner peripheral surface of boot 1600 which are configured to provide electrical continuity to the jaw members 110 and 120. The leads 1610a-1610f may be co-extruded or insert molded to the inner periphery of the boot 1600. At least one of the leads 1610a-1610h may be configured to carry or transmit a first electrical potential and at least one of the leads 1610a-1610h may be configured to carry a second electrical potential.

FIG. 16 shows yet another version of an insulating sheath or boot 1700 which is configured to be removable prior to insertion through a cannula (not shown). Boot 1700 is designed like a condom and is filled with a silicone lube 1710 and placed over the distal end of jaw members 110 and 120. Prior to insertion of the forceps 10 through a cannula, the boot 1700 is removed leaving residual silicone 1710 to facilitate insertion through the cannula. The forceps 10 may also include a second insulating boot 500 to reduce current concentrations similar to any one of the aforementioned embodiments or other embodiments described herein.

The present disclosure also relates to a method of facilitating insertion of a forceps through a cannula and includes the steps of providing a forceps including a shaft having a pair of jaw members at a distal end thereof. The jaw members are movable about a pivot from a first position wherein the jaw members are disposed in spaced relation relative to one another to a second position wherein the jaw members are closer to one another for grasping tissue. At least one of the jaw members is adapted to connect to a source of electrical energy such that the at least one jaw member is capable of conducting energy to tissue held therebetween. An insulative sheath is disposed atop at least a portion of an exterior surface of at least one jaw member, about the pivot and the distal end of the shaft. The insulative sheath houses a silicone lube configured to facilitate insertion of the forceps through a cannula after removal of the insulative sheath.

The method also includes the steps of removing the insulative sheath to expose the silicone lube atop the exterior surface of at least one jaw member, about the pivot and the distal end of the shaft, engaging the forceps for insertion through a cannula and inserting the forceps through the cannula utilizing the silicone lube to facilitate insertion.

FIGS. 17A and 17B show still another embodiment of the insulating boot 1800 which is configured as elastomeric shields 1800a and 1800b which are overmolded atop the proximal ends of respective jaw members 110 and 120 during a manufacturing step. A retention element (e.g., mechanical interface 1110) may also be included which engages one or both shields 1800a, 1800b. Once the forceps 10 is assembled, the elastomeric shields 1800a and 1800b are configured to abut one another to reduce stray current concentrations. FIGS. 18A and 18B show a similar version of an insulating boot 1900 which includes two overmolded elastomeric shields 1900a and 1900b which are mechanically engaged to one another by virtue of one or more weather strips 1910a and 1910b. More particularly, the weather strips 1910a and 1910b are configured to engage and seal the two opposing shields 1900a and 1900b on respective jaw members 110 and 120 during the range of motion of the two jaw members 110 and 120 relative to one another.

FIGS. 19A and 19B show yet another embodiment of the insulating boot 2000 which includes an elastomeric or silicone boot similar to boot 500 wherein the outer periphery of the boot 2000 includes a plurality of ribs 2010a-2010h which extend along the length thereof. It is contemplated that the ribs 2010a-2010h reduce the contact area of the boot 2000 with the inner periphery of a cannula (not shown) to reduce the overall surface friction of the boot during insertion into and withdrawal from the cannula.

FIG. 20 shows still another embodiment of the insulating boot 2100 which includes a soft caulk or putty-like material 2110 formed atop or within the boot which is configured to encapsulate the moving parts of the forceps 10. As best shown in FIG. 21, an overmolded section 114' may be formed over the proximal flange 113 of the jaw members, e.g., jaw member 110, to provide a rest for the insulating boot 500 (or any other version described above).

FIGS. 22A and 22B show yet another embodiment of an insulating boot 2200 which includes a plastic wedge-like material 2210 formed between the boot 2200 and the proximal ends 110' and 120' of the jaw members, e.g., jaw member 110 and jaw member 120, respectively. As best illustrated in the cross-section view of FIG. 22B, the plastic wedge-like material forms an upper wedge 2210a and a lower wedge 2210b that are configured to allow a range of motion of the jaw members 110 and 120 while keeping the boot 2200 intact atop the shaft 12 and the moving flanges 113 and 123 of the jaw members 110 and 120, respectively.

FIGS. 23A and 23B show still another envisioned embodiment of an insulating boot 2300 which includes an outer silicone-like shell 2310 which is dimensioned to house a layer of high resistance adhesive material 2320. If high current flowing through the insulating boot 2300 causes a rupture in the boot 2300, the adhesive material 2320 melts and flows through the ruptured portion to reduce the chances of current leakage during activation. FIGS. 24A and 24B show a similar insulative boot 2400 wherein the insulative boot 2400 includes a free flowing material which is designed to flow through the ruptured portion to provide additional insulation from current during activation. More particularly, the boot 2400 includes an internal cavity 2410 defined therein which retains a free-flowing material 2420. The free-flowing material 2420 is configured to disperse from the internal cavity 2410 when ruptured. The free-flowing material 2420 may be a high resistive adhesive, a lubricating material or an insulating material or combinations thereof. The internal cavity 2410 may be annular and disposed on a portion or the boot 2400 or may be longitudinal and disposed along a portion of the boot 2400. The free-flowing material 2420 may be configured to change state between a solid state and a liquid state upon the application of energy (e.g., heat energy) or light (e.g., ultraviolet). The free-flowing material 2420 may be disposed on either the distal and/or proximal ends of the flexible insulating boot 2400.

FIG. 25 shows yet another embodiment of the insulting boot 2500 wherein the distal end of the shaft 12 and the jaw members 110 and 120 are overmolded during manufacturing with a silicone material (or the like) to protect against stray current leakage during activation.

FIGS. 26A, 26B and 27 show other embodiments of an insulating boots 2600 and 2700, respectively, wherein boots 2600 and 2700 include low durometer portions and high durometer portions. The boots 2600 and 2700 may be formed from a two-shot manufacturing process. More particularly, FIGS. 26A and 26B include a boot 2600 with a high durometer portion 2610 having an elongated slot of low durometer material 2620 disposed therein or therealong. The low durometer portion 2620 is dimensioned to encapsulate the moving flanges 113 and 123 of the jaw members 110 and 120, respectively. FIG. 27 shows another embodiment wherein a ring of high durometer material 2710 is disposed at the distal end of the boot 2700 for radial retention of the jaw members 110 and 120. The remainder of the boot 2700 consists of low durometer material 2720.

FIG. 28 shows another embodiment of the present disclosure wherein the insulating boot 2800 may be packaged separately from the forceps 10 and designed to engage the end of the shaft 12 and jaw members 110 and 120 upon insertion though a cannula 2850. More particularly, boot 2800 may be packaged with the forceps 10 (or sold with the cannula 2850) and designed to insure 90 degree insertion of the forceps 10 through the cannula 2850. The boot 2800 in this instance may be made from silicone, plastic or other insulating material.

Figure 29B:
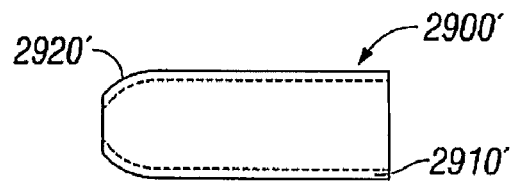

FIGS. 29A-29D include various embodiments of a boot 2900 having a tapered distal end 2920 and a straight proximal end 2910. More particularly, FIG. 29A shows a tapered bottle-like distal end 2920 which is configured to provide enhanced retentive force at the distal end of the forceps 10 which reduces the chances of the boot 2900 slipping from the boot's 2900 intended position. FIG. 29B shows another version of the tapered boot 2900' which includes a sharply tapered distal end 2920' and a straight proximal end 2910'.

Figure 29C:
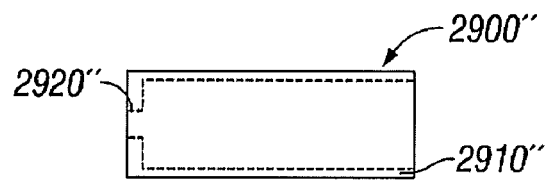
Figure 29D:
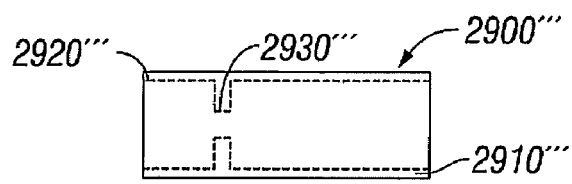

FIG. 29C shows another boot 2900" which includes a square-like taper 2920" at the distal end thereof and a straight proximal end 2910". FIG. 29D shows yet another version of a tapered boot 2900''' which includes a square, tapered section 2930''' disposed between distal and proximal ends, 2920' and 2910''', respectively. The outer diameter of the insulating boot 2900 or the inner periphery of the insulating boot 2900 may include the tapered section.

FIG. 30 shows yet another embodiment of the presently disclosed boot 3000 which is configured to be utilized with a jaw member 110 having a proximal overmolded section 114' similar to the jaw members disclosed with respect to FIG. 21 above. More particularly, jaw member 110 includes proximal overmolded section 114' having a bump or protrusion 115' disposed thereon. Bump 115' is configured to mechanically cooperate with a corresponding portion 3010 of boot 3000 to enhance retention of the boot 3000 atop the jaw member 110.

FIG. 31 shows still another embodiment of an insulating boot 500 which includes a silicone (or similar) ring-like sleeve 3100 which is configured to engage and secure the boot 500 atop the shaft 12. FIG. 32 shows a similar boot 500 configuration wherein a pair of weather strips 3200a and 3200b are positioned to secure the boot 500 at the junction point between the end of shaft 12 and the proximal end of the jaw members 110 and 120.

FIGS. 33A-33B show yet another embodiment of a co-molded boot 3300 having a silicone portion 3305 and proximal and side portions 3310c, 3310a and 3310b made a thermoplastic material (or the like). The thermoplastic materials 3310a-3310c enhance the rigidity and durability of the boot 3300 when engaged atop the jaw members 110 and 120 and the shaft 12. Thermoplastic portions 3310a and 3310b may be dimensioned to receive and/or mate with the proximal flanges 113 and 123 of jaw members 110 and 120, respectively.

FIG. 34 shows yet another embodiment of an insulating boot having a silicone boot 3350 mounted under a plastic shell 3355. A heat shrink tubing (or the like) 3360 is included which overlaps at least a portion of the plastic shell 3355 and silicone boot 3350.

FIGS. 35A and 35B show still another embodiment of an insulating boot 3400 which includes an overmolded thermoplastic clevis 3410 disposed on an inner periphery thereof which is configured to enhance the mechanical engagement of the boot 3400 with the jaw members 110 and 120 and shaft 12. More particularly, the clevis 3410 includes a pair of fingers 3410a and 3410b which project inwardly to mechanically engage the proximal end of jaw members 110 and 120. The proximal end of the boot 3400 fits atop the end of shaft 12 much like the embodiments described above (See FIG. 35B). An outer shell 3402 is disposed atop the overmolded thermoplastic clevis 3410 to enhance the rigidity of the boot 3400. The clevis 3410 includes a channel 3412 defined between the two fingers 3410a and 3410b which facilitates movement of the jaw members 110 and 120.

FIG. 36 shows yet another embodiment of an insulating boot 3500 which is similar to boot 3400 described above with respect to FIGS. 35A and 35B and includes a thermoplastic clevis 3510 having a pair of fingers 3510a and 3510b which project inwardly to mechanically engage the proximal end of jaw members 110 and 120. Boot 3500 also includes outer thermoplastic portions 3520a and 3520b which are configured to further enhance the rigidity of the boot 3500 and act as a so-called "exoskeleton". A channel 3515 is defined between in the outer exoskeleton to facilitate movement of the jaw members 110 and 120. The two outer portions 3520a and 3520b also include a relief portion 3525 disposed therebetween which allows the boot 3500 to expand during the range of motion of jaw members 110 and 120.

FIG. 37 shows yet another embodiment of an insulating boot 3600 which includes a plurality of thermoplastic rails 3610a-3610d disposed along the outer periphery thereof. The rails 3610a-3610d may be formed during the manufacturing process by overmolding or co-extrusion and are configured to enhance the rigidity of the boot 3600 similar to the embodiment described above with respect to FIG. 19B.

FIGS. 38A-38D show still another embodiment of an insulating boot 3700 which includes a low durometer portion 3725 generally disposed at the proximal end 3720 thereof and a high durometer portion 3730 generally disposed at the distal end 3710 thereof. The high durometer portion 3730 may be configured to mechanically engage the low durometer portion 3725 or may be integrally associated therewith in a co-molding or over-molding process. The inner periphery 3750 of the high durometer portion 3730 is dimensioned to receive the flanges 113 and 123 of jaw members 110 and 120, respectively. The low durometer portion 3725 may be dimensioned to allow the proximal ends 113 and 123 of flanges to flex beyond the outer periphery of the shaft 12 during opening of the jaw members 110 and 120. It is also contemplated that the high durometer portion 3730 (or a combination of the high durometer portion 3730 and the low durometer portion 3725) may act to bias the jaw members 110 and 120 in a closed orientation.

FIGS. 39A-39D show yet another embodiment of an insulating boot 3800 which includes a low durometer portion 3825 and a high durometer portion 3830 generally disposed at the distal end 3810 thereof. The high durometer portion 3830 includes proximally-extending fingers 3820a and 3820b which define upper and lower slots 3840a and 3840b, respectively, dimensioned to receive upper and lower low durometer portions 3825a and 3825b, respectively. The inner periphery 3850 of the high durometer portion 3830 is dimensioned to receive flanges 113 and 123 of jaw members 110 and 120, respectively. It is also contemplated that the high durometer portion 3830 (or a combination of the high durometer portion 3830 and the low durometer portions 3825a and 3825b) may act to bias the jaw members 110 and 120 in a closed orientation.

FIG. 40 shows yet another version of an insulating boot 3900 which includes a pair of hook-like mechanical interfaces 3900a and 3900b which are designed to engage the jaw members 110 and 120 at one end (e.g., the hook ends 3905a and 3905b) and designed to engage the shaft 12 at the opposite ends 3908a and 3908b, respectively. More particularly, the boot 3900 includes a pair of rails or slots 3912a and 3912b defined in an outer periphery thereof which are dimensioned to receive the corresponding hook-like mechanical interfaces 3900a and 3900b therealong. The proximal ends 3908a and 3908b of the hook-like mechanical interfaces 3900a and 3900b are configured to secure about the shaft 12 during an initial manufacturing step and then are held in place via the employment of heat shrink wrapping 12'. The heat shrink wrapping 12' prevents the hook-like mechanical interfaces 3900a and 3900b from slipping during insertion and removal of the forceps 10 through a cannula.

FIG. 41 shows still another version of an insulating boot 4000 which includes a series of pores 4010a-4010f disposed along the outer periphery thereof. A heat-activated adhesive or lubricant 4030 is included in the pores 4010a-4010f such that when the lubricant 4030 is heated, the lubricant 4030 flows freely over the boot 4000 thereby facilitating insertion and withdrawal of the forceps 10 from a cannula.

FIG. 42 shows still another embodiment of an insulating boot 500 which includes a strip of heat activated adhesive 4100 to secure the boot 500 to the jaw members 110 and 120. The heat activated adhesive 4100 is designed to cure upon the application of heat to prevent unwanted motion between the two jaw members 110 and 120 or between the jaw members 110 and 120 and the shaft 12. FIG. 43 shows similar concept which includes an insulating boot 4200 having a pair of overlapping flanges 4220a and 4220b which extend toward the jaw members 110 and 120 and which cooperate with one or more apertures (not shown) defined in the proximal flanges 113 and 123 of the jaw members 110 and 120 to retain a heat-activated adhesive 4230 therein. Once heated, the adhesive 4230 cures and maintains a strong, low profile bond between the boot 4200 and the jaw members 110 and 120.

FIGS. 44A and 44B show still another embodiment of an insulating boot 4300 which involves a two-step process for deployment atop the jaw members 110 and 120. During an initial manufacturing step the boot 4300 is in the form of an uncured adhesive sleeve 4300 and is fitted atop the proximal ends of the jaw members 110 and 120 and the shaft 12. Once properly positioned, the uncured adhesive sleeve 4300 is then cured using heat or UV light such that the cured boot 4300' creates a conformal coating atop the jaw members 110 and 120 and acts to secure the boot 4300' to the jaw members 110 and 120 and shaft 12 and insulate the surrounding tissue from negative electrical and thermal effects.

FIGS. 45A and 45B show still another embodiment of an insulating boot 4400 which also involves a two-step process for deployment atop the jaw members 110 and 120. During an initial manufacturing step the boot 4400 includes a ring of uncured adhesive material 4410 disposed along an inner periphery thereof. The boot 4400 with the uncured adhesive ring 4410 and is fitted atop the proximal ends of the jaw members 110 and 120 and the shaft 12. Once properly positioned, the uncured adhesive ring 4410 is then cured using heat or UV light such that the cured boot 4400' conforms atop the jaw members 110 and 120 and acts to secure the boot 4400' to the jaw members 110 and 120 and shaft 12.

FIG. 46 shows still another embodiment of the present disclosure which includes a coating 110' and 120' disposed on the exposed portions of the jaw members 110 and 120. The coating 110' and 120' may be made from an insulating material or made from a material that increases resistance with heat or current. The tip portion 111 of the jaw members 110 is exposed and does not include the coating material such that electrosurgical energy may be effectively transferred to tissue via the exposed tip portion 111.

As mentioned above, the insulating boot 500 may be from any type of visco-elastic, elastomeric or flexible material that is biocompatible and that is configured to minimally impede movement of the jaw members 110 and 120 from the open to closed positions. The insulating boot 1500 may also be made at least partially from a curable material which facilitates engagement atop the jaw members 110 and 120 and the shaft 12. The presently disclosed insulating boots 500-4400' described herein above may also be utilized with any of the forceps designs mentioned above for use with both endoscopic surgical procedures and open surgical procedures and both bipolar electrosurgical treatment of tissue (either by vessel sealing as described above or coagulation or cauterization with other similar instruments) and monopolar treatment of tissue.

The aforedescribed insulating boots, e.g., boot 500, unless otherwise noted, are generally configured to mount over the pivot, connecting jaw member 110 with jaw member 120. The insulating boots, e.g., boot 500, is flexible to permit opening and closing of the jaw members 110 and 120 about the pivot.

From the foregoing and with reference to the various figure drawings, those skilled in the art will appreciate that certain modifications can also be made to the present disclosure without departing from the scope of the same. For example and although the general operating components and inter-cooperating relationships among these components have been generally described with respect to a vessel sealing forceps, other instruments may also be utilized that may be configured to include any of the aforedescribed insulating boots to allow a surgeon to safely and selectively treat tissue in both a bipolar and monopolar fashion. Such instruments include, for example, bipolar grasping and coagulating instruments, cauterizing instruments, bipolar scissors, etc.

Furthermore, those skilled in the art recognize that while the insulating boots described herein are generally tubular, the cross-section of the boots may assume substantially any shape such as, but not limited to, an oval, a circle, a square, or a rectangle, and also include irregular shapes necessary to cover at least a portion of the jaw members and the associated elements such as the pivot pins and jaw protrusions, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
    a shaft having a pair of jaw members at a distal end thereof, the jaw members being movable about a pivot from a first position wherein the jaw members are disposed in spaced relation relative to one another to a second position wherein the jaw members are closer to one another for grasping tissue;
    a movable handle that actuates a drive assembly to move the jaw members relative to one another;
    at least one of the jaw members being adapted to connect to a source of electrical energy such that the at least one jaw member is capable of conducting energy to tissue held between the pair of jaw members; and
    a removable insulative sheath enclosing: at least one of the jaw members; at least a portion of the pivot; and at least a portion of the distal end of the shaft; the removable insulative sheath including a silicone lube disposed therein configured to remain on at least a portion of the forceps when the insulative sheath is removed therefrom, the silicone lube configured to facilitate insertion of the forceps through a cannula after removal of the insulative sheath.

2. The electrosurgical forceps according to claim 1 wherein the removable insulative sheath encloses both jaw members.

3. The electrosurgical forceps according to claim 1 wherein the removable insulative sheath encloses both jaw members, the pivot and at least a portion of the shaft.

4. The electrosurgical forceps according to claim 1, further including an insulating boot disposed on at least a portion of an exterior surface of at least one jaw member and circumferentially around at least a portion of the pivot.

5. The electrosurgical forceps according to claim 4, wherein the insulating boot is disposed between the insulative sheath and the pivot.

6. A method of facilitating insertion of a forceps through a cannula comprising the steps of:

providing a forceps including:

a shaft having a pair of jaw members at a distal end thereof, the jaw members being movable about a pivot from a first position wherein the jaw members are disposed in spaced relation relative to one another to a second position wherein the jaw members are closer to one another for grasping tissue;

at least one of the jaw members being adapted to connect to a source of electrical energy such that the at least one jaw member is capable of conducting energy to tissue held between the pair of jaw members;

a removable insulative sheath enclosing: at least one of the jaw members; at least a portion of the pivot and at least a portion of the distal end of the shaft; the removable insulative sheath including a silicone lube disposed therein configured to remain on at least a portion of the forceps when the insulative sheath is removed therefrom, the silicone lube configured to facilitate insertion of the forceps through a cannula after removal of the removable insulative sheath;

removing the removable insulative sheath, at least a portion of the silicone lube remaining on at least one of the at least one jaw member, the pivot and the distal end of the shaft;

engaging the forceps for insertion through a cannula; and inserting the forceps through the cannula utilizing the silicone lube to facilitate insertion.

7. The electrosurgical forceps according to claim 6 wherein the step of removing the insulative sheath occurs prior to the step of inserting the forceps through the cannula.

8. The electrosurgical forceps according to claim 6, further including an insulating boot disposed on at least a portion of an exterior surface of at least one jaw member and disposed circumferentially around at least a portion of the pivot.

9. The electrosurgical forceps according to claim 8, wherein the insulating boot is disposed between the insulative sheath and the pivot.

10. The electrosurgical forceps according to claim 8, wherein at least a portion of the silicone lube remains on the insulating boot when the insulating sheath is removed.

* * * * *